(12) United States Patent
Kimura et al.

(10) Patent No.: US 8,173,360 B2
(45) Date of Patent: May 8, 2012

(54) CELL DEATH INHIBITOR

(75) Inventors: Haruhide Kimura, Ibaraki (JP); Yoshimi Sato, Ibaraki (JP); Masayauki Takizawa, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 70 days.

(21) Appl. No.: 12/576,232

(22) Filed: Oct. 8, 2009

(65) Prior Publication Data

US 2010/0099106 A1    Apr. 22, 2010

Related U.S. Application Data

(62) Division of application No. 10/512,587, filed as application No. PCT/JP03/05256 on Apr. 24, 2003, now abandoned.

(30) Foreign Application Priority Data

Apr. 26, 2002  (JP) ................................. 2002-127202

(51) Int. Cl.
- *C12Q 1/00* (2006.01)
- *C12Q 1/68* (2006.01)
- *G01N 33/53* (2006.01)

(52) U.S. Cl. ................. 435/4; 435/6.1; 435/7.1
(58) Field of Classification Search .................. None
See application file for complete search history.

(56) References Cited

U.S. PATENT DOCUMENTS

| 6,030,615 A | 2/2000 | Bucala et al. |
| 6,794,383 B2 | 9/2004 | Kimura et al. |
| 7,399,759 B2 | 7/2008 | Kajino et al. |
| 2009/0082343 A1 | 3/2009 | Kajino et al. |

FOREIGN PATENT DOCUMENTS

| EP | 1 424 336 | 6/2004 |
| JP | 09-500363 | 1/1997 |
| JP | 2001-527072 | 12/2001 |
| WO | WO-94/26307 | 11/1994 |
| WO | WO 9729635 A1 * | 8/1997 |
| WO | WO-99/33823 | 7/1999 |
| WO | WO-00/64400 | 11/2000 |
| WO | WO 0138566 A2 * | 5/2001 |
| WO | WO-02/07720 | 1/2002 |
| WO | WO-02/18356 | 3/2002 |
| WO | 02/079517 | 10/2002 |
| WO | WO-02/094203 | 11/2002 |
| WO | WO-03/020719 | 3/2003 |

OTHER PUBLICATIONS

Rupreht et al., 2000, Pflugers Arch Eur J Physiol., vol. 440: R78-R80.*
Meyer et al., 1993, EMBO Journal, vol. 12: 2005-2015.*
Foresti et al., "Role of heme oxygenase-1 in hypoxia-reoxygenation: requirement of substrate heme to promote cardioprotection", Am J Physiol Heart Circ Physiol, vol. 281, pp. H1976-H1984 (2001).
Hangaishi et al., "Induction of Heme Oxygenase-1 Can Act Protectively against Cardiac Ischemia/Reperfusion in Vivo", Biochemical and Biophysical Research Communications, vol. 279, No. 2, pp. 582-588 (2000).
Hangaishi et al., "Regulation and Physiological Role of Cardiac Heme Oxygenase-1 after Cardiac Ischemia/Reperfusion in Rat", Japanese Circulation Journal, vol. 65, No. Supplement 1-A, p. 80 (2001).
Kobayashi et al., "Molecular Mechanisms for Free Radicals Nrf2 and Small Maf Family Transcription Factors", vol. 6, No. 2, pp. 100-107 (Jan. 3, 2002).
Pennock et al., "Interaction of macrophage-migration-inhibitory factor with haematin", Biochem J. 331, pp. 905-908 (1998).
Yamanaka et al., "Amlodipine Suppresses Doxorubicin-Induced Myocardial Cell Apoptosis", Japanese Circulation Journal, vol. 164, No. Supplement 1, p. 235 (2000).
Tanaka et al., "Anti-apoptotic effect of atorvastatin, a HMG-CoA reductase inhibitor, on cardiac myocyte via PXC activation", Circulation Journal, vol. 66, No. Supplement 1, p. 698, PJ-147 (2002).
Sakai et al., "Pravastatin reduces MMP-2 activity in an isolated rat heart after ischemia-reperfusion", Circulation Journal, vol. 66, No. Supplement 1, p. 698, PJ-148 (2002).
Kaneda et al., "Induction of Rat Vascular Endothelial Cell Apoptosis by HMG-CoA Reductase Inhibitors", 27[P]II H-337, vol. 122, No. 4, p. 32 (Mar. 5, 2002).
Japanese Office Action dated Aug. 25, 2009 in corresponding Japanese patent application No. 2003-119153.
The Supplementary European Search Report and European Search Opinion dated Nov. 27, 2009, from corresponding European application No. 03719195.4.
Lue et al., "Macrophage Migration Inhibitory Factor (MIF): Mechanisms of Action and Role in Disease", Microbes and Infection, vol. 4, Jan. 1, 2002, pp. 449-460.
"Business Wire: IDEC Pharmaceuticals and Taisho Announce Collaborative Agreement to Develop Antibodies Targeting Inflammatory & Autoimmune diseases", Jun. 28, 2000, Retrieved from the Internet: URL:http://findarticles.com/p/articles/mi_mOEIN/is_2000_June_28/ai_63021129/> [retrieved on Nov. 13, 2009].
Business Wire: "IDEC Pharmaceuticals Reports Second Quarter 2000 Results", Jun. 18, 2000, Retrieved from the Internet: URL:http://www.thefreelibrary.com/_/print/PrintArticle.aspx?id=63545560> [retrieved on Nov. 13, 2009].
Calandra et al., "Protection from septic shock by neutralization of macrophage migration inhibitory factor", Nature Medicine, Feb. 2000, vol. 6, No. 2, Feb. 2000, pp. 164-170.

(Continued)

*Primary Examiner* — Amy Juedes
(74) *Attorney, Agent, or Firm* — Edwards Wildman Palmer LLP; David G. Conlin; Mark D. Russett

(57) ABSTRACT

The cell death inhibitor comprising a substance capable of binding to macrophage migration inhibitory factor is useful as a preventive/therapeutic agent for, e.g., heart diseases, neurodegenerative diseases, cerebrovascular diseases, central nervous infections, traumatic diseases, demyelinating diseases, bone/joint diseases, kidney diseases, liver diseases, myelodysplastic diseases, arteriosclerosis, diabetes, pulmonary hypertension, sepsis, inflammatory bowel diseases, autoimmune diseases, failure accompanying rejection in organ transplantation, AIDS, cancer, etc.

3 Claims, 8 Drawing Sheets

OTHER PUBLICATIONS

"United States Securities and Exchange Commission, Form 10-K, IDEC Pharmaceuticals Corporation, Annual Report on Form 10-K for the Fiscal Year Ended Dec. 31, 2000", Mar. 28, 2001, Retrieved from the Internet: URL:http://www.123jump.com/10K_Reports/BIIB/2001/2001.;htm> [retrieved on Nov. 13, 2009].

"United States Securities and Exchange Commission, Form 10-K, Annual Report, IDEC Pharmaceutical Corporation", Mar. 28, 2001, Retrieved from the Internet: URL:http://google.brand.edgar-online.com/EFX_dll/EDGARpro.dll?FetchFilingHTML1?ID=261650&SessionID=f7aiWWRH7jOd-m7> [retrieved on Nov. 13, 2009].

Mitchell et al., "Sustained mitogen-activated protein kinase (MAPK) and cytoplasmic phospholipase A2 activation by macrophage migration inhibitory factor (MIF). Regulatory role in cell proliferation and glucocorticoid action", The Journal of Biological Chemistry Jun. 18, 1999, vol. 274, No. 25, Jun. 18, 1999, pp. 18100-18106.

Leech et al., "Macrophage migration inhibitory factor in rheumatoid arthritis: Evidence of proinflammatory function and regulation by glucocorticoids", Arthritis and Rheumatism, vol. 42, No. 8, Aug. 1, 1999, pp. 1601-1608.

Lan et al., "The pathogenic role of macrophage migration inhibitory factor in immunologically induced kidney disease in the rat", The Journal of Experimental Medicine Apr. 21, 1997, vol. 185, No. 8, Apr. 21, 1997, pp. 1455-1465.

Donnelly et al., "Regulatory role for macrophage migration inhibitory factor in acute respiratory distress syndrome", Nature Medicine Mar. 1997, vol. 3, No. 3, Mar. 1997, pp. 320-323.

Mikulowska et al., "Macrophage migration inhibitory factor is involved in the pathogenesis of collagen type II-induced arthritis in mice", Journal of Immunology, Jun. 1, 1997, vol. 158, No. 11, pp. 5514-5517.

Orita et al., "Coumarin and Chromen-4-one Analogues as Tautomerase Inhibitors of Macrophage Migration Inhibitory Factor: Discovery and X-ray Crystallography", J. Med. Chem. 44(4): 540-547 (2001).

Zhang et al., "Inhibition of Macrophage Migration Inhibitory Factor (MIF) Tautomerase Activity by Dopachrome Analogs", Bioorganic & Medicinal Chemistry Letters 9(22): 3193-3198 (1999).

European Search Report dated Oct. 15, 2010, in corresponding European Patent Application No. 10177481.8.

Santos et al., Role of macrophage migration inhibitor factor in murine antigen-induced arthritis: interaction with glucocorticoids. Clin. Exp. Immunol. vol. 123: 309-314, 2001.

Calandra et al., "Protection from septic shock by neutralization of macrophage migration inhibitory factor," Nature Medicine, 6(2):164-170 (2000).

Takahashi et al., "Antisense Macrophage Migration Inhibitory Factor: (MIF) Prevents Anti-IgM Mediated Growth Arrest and Apoptosis of a Murine B Cell Line by Regulating Cell Cycle Progression," Microbiol. Immunol., 43(1):61-67 (1999).

Abe et al., "Regulation of the CTL Response by Macrophage Migration Inhibitory Factor," J. Immunol., 166:747-753 (2001).

Pennock et al., "Interaction of macrophage-migration-inhibitory factor with haematin," Biochem. J., 331:905-908 (1998).

Nishihira, J., "Novel pathophysiological aspects of macrophage migration inhibitory factor," Int. J. Mol. Med., 2:17-28 (1998).

International Search Report from corresponding PCT Application No. PCT/JP03/05256 (with English translation), 2004.

International Preliminary Examination Report (English translation) from corresponding PCT Application No. PCT/JP03/05256, 2003.

FDA Consumer Magazine, "Alzheimer's:Searching for a Cure", pp. 1-7 (2003).

Zhang et al., Biochem. and Biophys. Res. Comm., vol. 342:671-679 (2006).

Fichtner-Feigl et al., J. Clin. Invest., vol. 115, pp. 3057-3071 (2005).

Kimura et al., Cardiomyocyte apoptosis inhibitors and prophylactic/therapeutic agents for cardiac disease (translation of WO0218356), pp. 1-35, 2006.

* cited by examiner

CELL DEATH INHIBITOR

CROSS-REFERENCE TO RELATED APPLICATIONS

This application is a divisional application of U.S. application Ser. No. 10/512,587, filed Oct. 25, 2004, which is a U.S. national phase application under 35 U.S.C. §371 of International Application Serial No. PCT/JP03/05256, filed Apr. 24, 2003, which claims the benefit of Japanese Application Serial No. 2002-127202, filed Apr. 26, 2002. The entire contents of all of the above-referenced applications are incorporated herein by this reference.

TECHNICAL FIELD

The present invention relates to a cell death inhibitor, screening for the cell death inhibitor, and the like.

BACKGROUND ART

From the nature of processes to death, cell death is categorized into two types, necrosis and apoptosis. Necrosis is accidental cell death that accidentally occurs due to physical/chemical factors, etc. In contrast, apoptosis is cell death deeply involved in morphogenesis during the developmental process, tissue formation, maintenance of homeostasis, biological defense, etc. to play a critical role in supporting the individual's life, and the process is regulated by a gene. Congenital or acquired disorders of these cell death processes excessively induce or prevent cell death to cause dysfunctions of various organs, leading to diseases (SAISHIN-IGAKU, 54, 825, 1999).

In recent years, it has been revealed that these types of cell death are deeply committed to the development or progress of various diseases (R. Sanders Williams, The New England Journal of Medicine, 341, 759, 1999). For example, diseases caused by increased cell death include neurodegenerative diseases (e.g., Alzheimer's disease, Parkinson's disease, amyotrophic lateral sclerosis, retinitis pigmentosa, cerebellar degeneration, etc.), ischemic diseases (e.g., myocardial infarction, heart failure, apoplexy, cerebral infarction, ischemic acute renal failure, etc.), bone/joint diseases (e.g., osteoporosis, arthritis deformans, rheumatism, etc.), myelodysplastic diseases (e.g., aplastic anemia, etc.), hepatic diseases (e.g., alcoholic hepatitis, viral hepatitis, etc.), diabetes mellitus, AIDS, etc. [Nippon Rinsho, 54, 1996; Extra Issue: Igaku-no-Ayumi, page 8, 1997, etc.].

Macrophage migration inhibitory factor (MIF) is an inflammatory cytokine produced from immunopathologically mediated cells, hypophysis, etc. in concert with an invasion into the body, and are known to be located upstream of the inflammatory cytokine cascade to control inflammatory responses (Annual Reports in Medicinal Chemistry, 33, 24, 1998; Advances in Immunology, 66, 197, 1997). Furthermore, it is becoming clear that MIF is involved in the proliferation and differentiation of fat cells, cancer cells, etc. and plays an important role not only in immune response but also in various biological reactions (International Journal of Molecular Medicine, 2, 17, 1998). As the cells/tissues which express MIF, the following are known: T cells, monocytes/macrophages, mesangial cells, tubular epithelial cells, corneal epithelial cells, hepatocytes, oocytes, Sertoli cell, keratinocytes, osteoblasts, synovial cells, fat cells, astrocytes, cancer cells, mucous membranes, hypophysis, etc. As examples for MIF to take part in human diseases, there are reports showing that MIF level markedly increased in synovial fluid or serum from the patient with rheumatism, in alveolar lavage fluid from the patient with acute respiratory distress syndrome, in urine collected during rejection from the patient who received a kidney transplant, and in serum from the patient with acute myocardial infarction, diabetes mellitus, systemic lupus erythematosus, Crohn's disease or atopic dermatitis, when compared to healthy individuals. As an example that suppression of MIF leads palliation of symptoms, there is an experiment using anti-MIF neutralizing antibody. That is, in animal disease model of nephritis, hepatitis, pneumonia, arthritis, endotoxin shock, etc., markedly improving effects are observed in the group administered with anti-MIF neutralizing antibody (International Journal of Molecular Medicine, 2, 17, 1998).

As to the relationship between this MIF and cell death, it is reported that apoptosis mediated by anti-IgM antibody in a mouse B cell line is inhibited by reduced production of MIF (Microbiology and Immunology, 43, 61, 1999). However, the relationship between MIF and cell death is unknown except for the mouse B cell line, and moreover, there is no report on mechanism of cell death in which MIF is involved.

Recently factors controlling induction of apoptosis have been revealed one after another with the development of studies on cell death, especially studies on apoptosis. As a result, many attempts to directly repress apoptosis have been made using low molecular weight compounds which were searched for targeting these controlling factors. Among others, caspase inhibitors targeting caspase, which work on the final stage of apoptosis, have been actively studied, but any of them has not been clinically applied [JIKKEN IGAKU (Experimental Medicine), 19, 1726, 2001]. Also with necrosis, studies have been made on chaperones such as HSP70, etc. but clinical application has not been made yet (Essays in Biochemistry, 32, 17, 1997). For these reasons, it has been earnestly desired to develop a safe and potent cell death inhibitor and a screening system for searching the cell death inhibitor.

DISCLOSURE OF THE INVENTION

In view of the foregoing situations, the present inventors have made extensive studies and as a result, found that monoclonal antibodies against macrophage migration inhibitory factors (MIF), low molecular compounds capable of binding to MIF and the like prevent serum depletion-induced cell death in rat primary cardiomyocytes. Furthermore, the inventors have found that low molecular compounds capable of binding to this MIF prevent myocardial cell death induced by doxorubicin or HMG-CoA reductase inhibitors, cartilage cell death induced by NO, etc. and have also found that the low molecular compounds increase expression of genes under control of Antioxidant response element (ARE). Based on these findings, the inventors have continued further investigations and come to accomplish the present invention.

That is, the present invention relates to the following features and the like.

(1) A cell death inhibitor comprising a substance capable of binding to macrophage migration inhibitory factor.

(2) The cell death inhibitor according to (1), wherein the substance capable of binding to macrophage migration inhibitory factor is an antibody against the macrophage migration inhibitory factor.

(3) The cell death inhibitor according to (2), wherein the antibody is a monoclonal antibody.

(3a) The cell death inhibitor according to (3), wherein the monoclonal antibody is a monoclonal antibody named BWS48-1a which can be produced from a hybridoma named BWS48-1 (FERM BP-7991).

(4) The cell death inhibitor according to (1), wherein the substance capable of binding to macrophage migration inhibitory factor is a compound represented by the formula:

$$\text{[benzothiazinone structure with substituent R]}$$

wherein R represents a hydrocarbon group which may optionally have a substituent(s), an aromatic heterocyclic group which may optionally have a substituent(s), or an amino which may optionally have a substituent(s), or a salt thereof.

(5) The cell death inhibitor according to (1), wherein the substance capable of binding to macrophage migration inhibitory factor is a metalloporphyrin.

(5a) The cell death inhibitor according to (5), wherein the metalloporphyrin is hemin or hematin.

(6) The cell death inhibitor according to (1), wherein the substance capable of binding to macrophage migration inhibitory factor is a substance promoting expression of a gene under control of Antioxidant response element.

(6a) The cell death inhibitor according to (6), wherein the gene under control of Antioxidant response element is Heme oxygenase-1, Liver glutathione S-transferase Ya subunit, Liver glutathione S-transferase Yc subunit, Glutathione S-transferase Yb subunit, Glutathione S-transferase Yc1 subunit, Gamma-glutamylcysteine synthetase, NAD(P)H:quinone reductase, UDP-glucuronosyltransferase, exon 1, Bilirunin-specific UDP-glucuronosyltransferase, or NAD(P)H-menadione oxidereductase.

(6b) The cell death inhibitor according to (6), wherein the gene under control of Antioxidant response element is Heme oxygenase-1.

(7) The cell death inhibitor according to (1), wherein the substance capable of binding to macrophage migration inhibitory factor is a substance enhancing the production of a gene protein under control of Antioxidant response element.

(7a) The cell death inhibitor according to (7), wherein the gene under control of Antioxidant response element is Heme oxygenase-1, Liver glutathione S-transferase Ya subunit, Liver glutathione S-transferase Yc subunit, Glutathione S-transferase Yb subunit, Glutathione S-transferase Yc1 subunit, Gamma-glutamylcysteine synthetase, NAD(P)H:quinone reductase, UDP-glucuronosyltransferase, exon 1, Bilirunin-specific UDP-glucuronosyltransferase, or NAD(P)H-menadione oxidereductase.

(7b) The cell death inhibitor according to (7), wherein the gene under control of Antioxidant response element is Heme oxygenase-1.

(8) The cell death inhibitor according to (1), wherein the substance capable of binding to macrophage migration inhibitory factor is a substance promoting the activity of a gene protein under control of Antioxidant response element.

(8a) The cell death inhibitor according to (8), wherein the gene under control of Antioxidant response element is Heme oxygenase-1, Liver glutathione S-transferase Ya subunit, Liver glutathione S-transferase Yc subunit, Glutathione S-transferase Yb subunit, Glutathione S-transferase Yc1 subunit, Gamma-glutamylcysteine synthetase, NAD(P)H:quinone reductase, UDP-glucuronosyltransferase, exon 1, Bilirunin-specific UDP-glucuronosyltransferase, or NAD(P)H-menadione oxidereductase.

(8b) The cell death inhibitor according to (8), wherein the gene under control of Antioxidant response element is Heme oxygenase-1.

(9) A method of screening a cell death inhibitor, which comprises usingmacrophage migration inhibitory factor.

(10) The screening method according to (9), wherein the cell death inhibitor is a substance promoting the expression of a gene under control of Antioxidant response element.

(11) The screening method according to (9), wherein (i) in case that macrophage migration inhibitory factor is mixed with a labeled compound capable of binding to macrophage migration inhibitory factor and (ii) in case that a test compound and macrophage migration inhibitory factor are mixed with the labeled compound capable of binding to macrophage migration inhibitory factor, the binding amounts of the labeled compounds bound to macrophage migration inhibitory factor are measured in each case, and comparison is made therebetween.

(12) A kit for screening a cell death inhibitor, comprising macrophage migration inhibitory factor.

(13) A method for quantification of macrophage migration inhibitory factor, which comprises using a substance capable of binding to macrophage migration inhibitory factor.

(14) A method for diagnosis of diseases associated with macrophage migration inhibitory factor, which comprises using the method for quantification according to (13).

(14a) The method for diagnosis according to (14), wherein the diseases are heart diseases, neurodegenerative diseases, cerebrovascular diseases, central nervous infections, traumatic diseases, demyelinating diseases, bone/joint diseases, kidney diseases, liver diseases, myelodysplastic diseases, arteriosclerosis, diabetes, pulmonary hypertension, sepsis, inflammatory bowel diseases, autoimmune diseases, AIDS or cancer.

(15) The cell death inhibitor according to (1), which is an agent for the prevention/treatment of heart diseases, neurodegenerative diseases, cerebrovascular diseases, central nervous infections, traumatic diseases, demyelinating diseases, bone/joint diseases, kidney diseases, liver diseases, myelodysplastic diseases, arteriosclerosis, diabetes, pulmonary hypertension, sepsis, inflammatory bowel diseases, autoimmune diseases, failure accompanying rejection in organ transplantation, AIDS or cancer, or an agent for protecting transplant organs.

(16) The cell death inhibitor according to (1), which is an agent for the prevention/treatment of inflammatory bowel diseases.

(17) The cell death inhibitor according to (1), wherein a HMG-CoA reductase inhibitor, a fibrate-type antihyperlipidemic drug and/or an anticancer agent are/is used in combination.

(18) A method of inhibiting cell death, which comprises administering to a mammal an effective dose of a substance capable of binding to macrophage migration inhibitory factor.

(18a) A method of preventing/treating inflammatory bowel diseases, which comprises administering to a mammal an effective dose of a substance capable of binding to macrophage migration inhibitory factor.

(19) Use of a substance capable of binding to macrophage migration inhibitory factor to manufacture a cell death inhibitor.

(19a) Use of a substance capable of binding to macrophage migration inhibitory factor to manufacture an agent for the prevention/treatment of inflammatory bowel diseases.

BEST MODE FOR CARRYING OUT THE INVENTION

Figure 1:
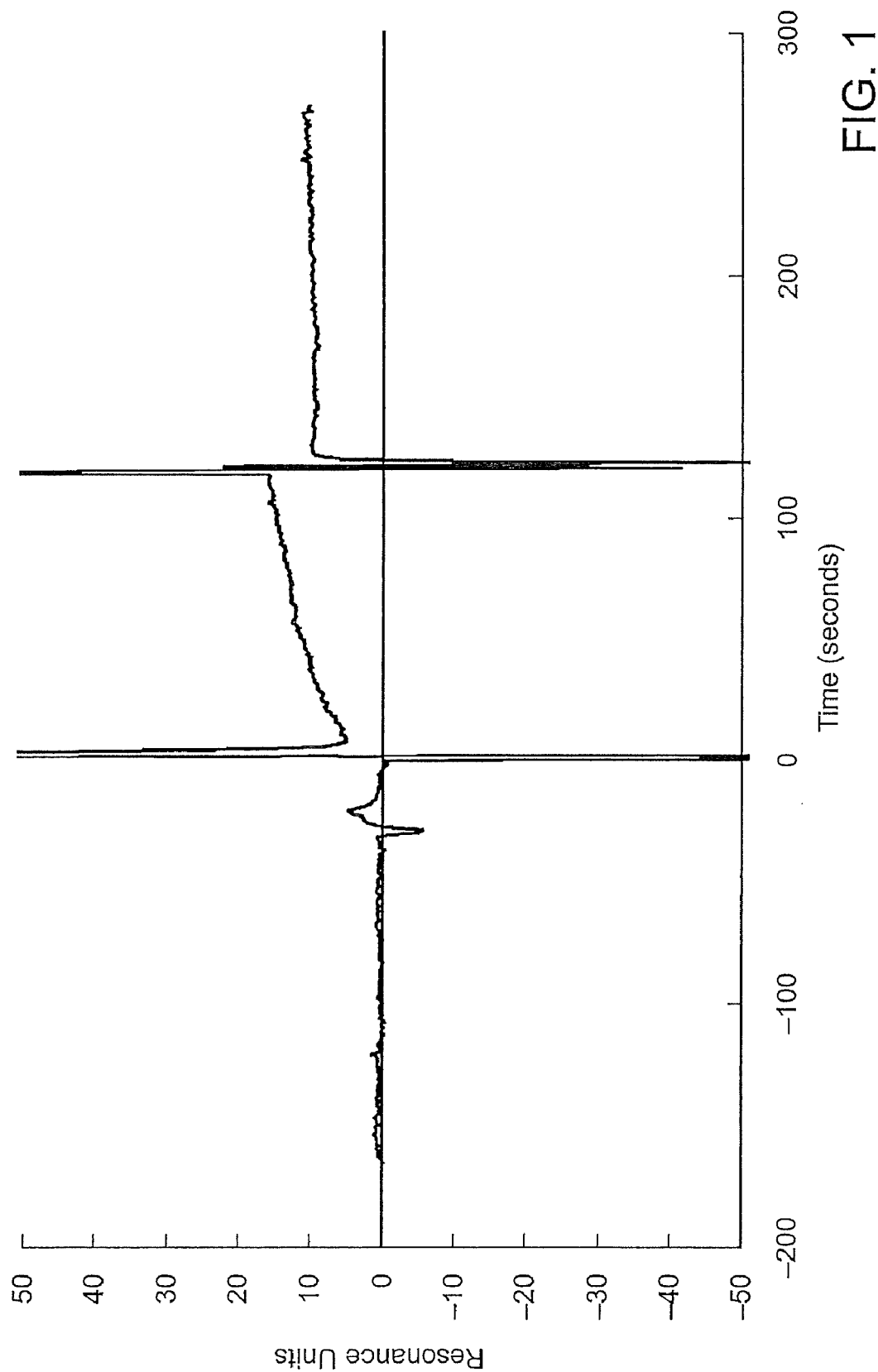
FIG. 1 shows the results of binding of MIF to Compound 1, wherein the ordinate represents the surface plasmon resonance signals (resonance units) and the abscissa represents time (seconds).

Any substance can be used as the substance capable of binding to macrophage migration inhibitory factor (MIF), so long as it is a substance capable of binding to MIF. It may be a substance that regulates the functions of MIF.

The substance capable of binding to MIF includes, for example, (a) antibodies against MIF, (b) compounds represented by the formula:

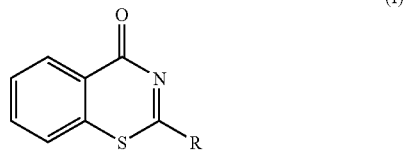

(I)

wherein R represents a hydrocarbon group which may optionally have a substituent(s), an aromatic heterocyclic group which may optionally have a substituent(s), or an amino which may optionally have a substituent(s, or salts thereof, (c) metalloporphyrins, (d) compounds described in WO 03/020719 or salts thereof, (e) compounds described in WO 02/094203 or salts thereof, etc.

The antibodies against MIF described in (a) above may be any of antibodies, as long as they specifically react with MIF and include polyclonal antibodies and monoclonal antibodies, with monoclonal antibodies being preferred. Specific and preferred examples are a monoclonal antibody named BWS48-1a, which can be produced from a hybridoma cell named BWS48-1 (FERM BP-7991), and the like.

The antibody can be manufactured using MIF as an antigen in accordance with publicly known methods of manufacturing antibodies or antisera.

[Preparation of Monoclonal Antibody]

(i) Preparation of Monoclonal Antibody-Producing Cells

MIF itself is administered solely or MIF is administered together with a carrier, a diluent, etc. to warm-blooded animal at the site where the antibody can be produced through administration. In order to facilitate the production of antibodies upon the administration, complete Freund's adjuvant or incomplete Freund's adjuvant may be administered. The administration may be usually conducted once per 2 to 6 weeks, and 2 to 10 times in total. Examples of the warm-blooded animal used may include monkey, rabbit, dog, guinea pig, mouse, rat, sheep, goat, and chicken. Mouse and rat may be preferably used.

Upon the preparation of monoclonal antibody-producing cells, an individual in which the antibody titer can be recognized is selected from the warm-blooded animals, e.g., mice that had been immunized with an antigen. On 2 to 5 days after final immunization, spleen or lymph node is collected, and the antibody-producing cells contained therein are fused with myeloma cells from an animal of the same or different species to effect the preparation of monoclonal antibody-producing hybridomas. The determination of the antibody titer in the antiserum may be carried out, for example, by reacting a labeled form of MIF with the antiserum, and assaying the activity of the label bound to the antibody. The fusion procedures can be performed in accordance with known methods, for example, the method of Köhler and Milstein [Nature, 256, 495, and (1975)]. Examples of the fusion accelerating agent include polyethylene glycol (PEG), Sendai virus and the like, and PEG may be preferably used.

The myeloma cell includes myeloma cells from the warm-blooded animal, for example, NS-1, P3U1, SP2/0, AP-1, etc., and P3U1 may be preferably used. The ratio of antibody producing cell (spleen cell) count to myeloma cell count preferably used is approximately 1:1 to 20:1. PEG (preferably, PEG1000-PEG6000) is added in a concentration of approximately 10 to 80%. The cell fusion can be efficiently performed through incubation at 20 to 40° C., preferably at 30 to 37° C. for 1 to 10 minutes.

Screening of the hybridoma that produces the monoclonal antibody can be performed by using various methods, including, for example, a method in which a supernatant of hybridoma culture is added to a solid phase (e.g., a microplate) on which a protein antigen is adsorbed directly or together with a carrier, and then an anti-immunoglobulin antibody (when the cell used for the cell fusion is derived from mouse, anti-mouse immunoglobulin antibody is used) that is labeled with a radioactive substance, enzyme or the like, or protein A is added thereto thereby detecting the monoclonal antibody bound to the solid phase; or a method in which a supernatant of hybridoma culture is added to a solid phase on which anti-immunoglobulin antibody or protein A is adsorbed, and then a protein labeled with a radioactive substance, enzyme or the like is added thereto thereby detecting the monoclonal antibody bound to the solid phase; and the like.

Selection of the monoclonal antibody can be carried out by publicly known methods, or those with modifications. Usually, the method can be carried out in a medium for animal cells with HAT (hypoxanthine, aminopterin, and thymidine) added. The medium for use in the selection and growing may be any one of the media in which hybridoma can grow. For example, RPMI medium containing 1 to 20%, preferably 10 to 20% of fetal bovine serum, GIT medium (Wako Pure Chemical Industries, Ltd.) containing 1 to 10% of fetal bovine serum, or serum-free medium for hybridoma culture (SFM-101, Nissui Pharmaceutical Co., Ltd.), and the like. The temperature of the culture is usually at 20 to 40° C., preferably about 37° C. The culture period is usually 5 days to 3 weeks, preferably 1 week to 2 weeks. The culture is usually carried out in 5% carbon dioxide gas. The antibody titer of the supernatant of the hybridoma culture can be assayed in a manner similar to the assay of the antibody titer in an antiserum as described above.

(ii) Purification of Monoclonal Antibody

The separation and purification of monoclonal antibody can be carried out according to publicly known methods, for example, methods for separation and purification of immunoglobulins [e.g., a salt precipitation method, an alcohol precipitation method, an isoelectric point precipitation method, an electrophoretic method, an adsorption/desorption method by an ion exchanger (e.g., DEAE), an ultracentrifugation method, a gel filtration method, and a specific purification method in which an antibody alone is collected by an antigen-bound solid phase or an active adsorbent such as protein A or protein G, or the like, and the binding is then dissociated to give the antibody].

[Preparation of Polyclonal Antibody]

The polyclonal antibody can be prepared by publicly known methods or those with modifications. For example, an immunoantigen (a protein antigen) itself or a complex, which is formed with the immunoantigen (protein antigen) and a carrier protein, is used for the immunization of a warm-blooded animal in a similar manner to the methods for preparing the monoclonal antibody described above, followed by collecting the product containing the desired antibody from the warm-blooded animal, and then the antibody is purified/isolated, whereby the polyclonal antibody can be prepared.

In regard to the complex of an immunoantigen and a carrier protein for use in the immunization of the warm-blooded animal, the kind of the carrier protein and the mixing ratio of the carrier and hapten may be optional, as long as the antibody can be efficiently produced against the hapten immunized after crosslinking with the carrier, and any kind of the carrier protein may be crosslinked at any ratio. For example, the method in which bovine serum albumin, bovine thyroglobulin, hemocyanin, etc., is coupled with hapten in a weight ratio of approximately 0.1 to 20, preferably approximately 1 to 5, based on 1 of the hapten, may be used.

In addition, a variety of condensing agents may be used for the coupling of the hapten and carrier, which include glutaraldehyde and carbodiimide, maleimide activated ester, and activated ester reagents containing thiol group, dithiopyridyl group; and the like.

The condensation product is administered solely or together with a carrier or a diluent to a warm-blooded animal at a site that enables the production of the antibody upon the administration. In order to facilitate the production of antibodies upon the administration, complete Freund's adjuvant or incomplete Freund's adjuvant may be administered. The administration may be usually conducted once per approximately 2 to 6 weeks, and approximately 3 to 10 times in total.

Polyclonal antibodies can be collected from the blood, ascites, etc., preferably from the blood, of the warm-blooded animal immunized by the method as described above.

The measurement of the antibody titer in antiserum can be carried out in a manner similar to the measurement of the antibody titer of the antiserum as described above. The separation and purification of the polyclonal antibody can be carried out according to the method for separation and purification of an immunoglobulin similarly to the method for separation and purification of a monoclonal antibody described above.

In the "hydrocarbon group which may optionally have a substituent(s)" as represented by R in the formula (I) of (b) described above, the "hydrocarbon group" includes, e.g., alkyl, cycloalkyl, cycloalkylalkyl, alkenyl, alkynyl, aryl, aralkyl, etc.

Examples of the "alkyl" include $C_{1-6}$ alkyl (e.g., methyl, ethyl, propyl, isopropyl, butyl, isobutyl, sec-butyl, tert-butyl, pentyl, hexyl, etc.), and the like.

Examples of the "cycloalkyl" include $C_{3-6}$ cycloalkyl (e.g., cyclopropyl, cyclobutyl, cyclopentyl, cyclohexyl, etc.), and the like.

Examples of the "cycloalkylalkyl" include a $C_{4-7}$ cycloalkylalkyl group (e.g., cyclopropylmethyl, cyclobutylmethyl, cyclopentylmethyl, cyclohexylmethyl, etc.), and the like.

Examples of the "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.), and the like.

Examples of the "alkynyl" include $C_{2-6}$ alkynyl (e.g., ethynyl, propargyl, 1-butynyl, 2-butynyl, 3-butynyl, 1-hexynyl, etc.), and the like.

Examples of the "aryl" include $C_{6-14}$ aryl (e.g., phenyl, naphthyl, biphenyl, indanyl, 1,2,3,4-tetrahydronaphthyl, etc.), and the like.

Examples of the "aralkyl" include $C_{7-16}$ aralkyl (e.g., benzyl, phenethyl, phenylpropyl, naphthylmethyl, indanylmethyl, etc.), and the like.

In the "hydrocarbon group which may optionally have a substituent(s)" as represented by R, examples of the "substituent(s)" include a halogen atom (e.g., fluorine, chlorine, bromine, iodine, etc.), an aromatic heterocyclic group, oxo, hydroxy, $C_{1-4}$ alkoxy (e.g., methoxy, ethoxy, propoxy, butoxy, etc.), carboxy, $C_{1-4}$ alkyl-carbonyl (e.g., acetyl, propionyl, etc.), $C_{6-14}$ aryl-carbonyl (e.g., benzoyl, etc.), $C_{1-4}$ alkoxy-carbonyl (e.g., methoxycarbonyl, ethoxycarbonyl, propoxycarbonyl, butoxycarbonyl, etc.), $C_{6-14}$ aryloxy-carbonyl (e.g., phenoxycarbonyl, etc.), $C_{7-16}$ aralkyloxy-carbonyl (e.g., benzyloxycarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), optionally halogenated $C_{6-14}$ aryl-carbamoyl, 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), and a 5- to 7-membered saturated cyclic amino-carbonyl which may optionally have a substituent(s), etc. Among them, $C_{6-14}$ aryl-carbonyl, $C_{1-4}$ alkoxy-carbonyl, 5- to 6-membered heterocyclic carbamoyl, and 5- to 7-membered saturated cyclic amino-carbonyl are preferred.

The "aromatic heterocyclic group" includes, for example, a monovalent group formed by removing one hydrogen atom from a 5- to 14-membered (preferably 5- to 10-membered) aromatic hetero-ring containing 1 to 4 hetero atoms of one or two species selected from a nitrogen atom, a sulfur atom and an oxygen atom, in addition to the carbon atoms. The "5- to 14-membered (preferably 5- to 10-membered) aromatic hetero-ring" includes, for example, aromatic hetero-rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, etc.; or rings formed by condensing any one of these rings (preferably a monocyclic ring) with one or more (preferably 1 or 2) aromatic rings (e.g., benzene ring, etc.).

Examples of the "aromatic heterocyclic group" include thienyl (e.g., 2-thienyl, 3-thienyl), furyl (e.g., 2-furyl, 3-furyl), pyridyl (e.g., 2-pyridyl, 3-pyridyl, 4-pyridyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 3-pyrrolyl), imidazolyl (e.g., 2-imidazolyl), pyridazinyl (e.g., 3-pyridazinyl), isothiazolyl (e.g., 3-isothiazolyl), isooxazolyl (e.g., 3-isooxazolyl), indolyl (e.g., 1-indolyl, 2-indolyl, 3-indolyl), benzothiazolyl (e.g., 2-benzothiazolyl), benzothienyl (e.g., 2-benzo[b]thienyl, 3-benzo[b]thienyl), benzofuranyl (e.g., 2-benzo[b]furanyl, 3-benzo[b]furanyl), etc. Among them, a 5- to 6-membered heterocyclic group containing 1 to 3 hetero atoms selected from a nitrogen atom, a sulfur atom and an oxygen atom, in addition to the carbon atoms (e.g., pyridyl such as 2-pyridyl, 3-pyridyl, 4-pyridyl) is preferred.

Examples of the "optionally halogenated $C_{6-14}$ aryl-carbamoyl" include $C_{6-14}$ aryl-carbamoyl (e.g., phenylcarbamoyl, 1-naphthylcarbamoyl and 2-naphthylcarbamoyl, etc.), which may optionally contain 1 to 3 halogen atoms (e.g., fluorine, chlorine, etc.).

In the "5- to 7-membered saturated cyclic amino-carbonyl which may optionally have a substituent(s)", the "5- to 7-membered saturated cyclic amino-carbonyl" includes, for example, pyrrolidin-1-ylcarbonyl, piperidinocarbonyl, piperazin-1-ylcarbonyl, morpholinocarbonyl, etc. Examples of the "substituent(s)" in the "5- to 7-membered saturated cyclic amino-carbonyl which may optionally have a substituent(s)" include one or two $C_{1-3}$ alkyl (e.g., methyl, etc.), phenyl, benzyl, etc.

The "hydrocarbon group which may optionally have a substituent(s)" may have, for example, 1 to 5, preferably 1 to 3, of the substituents at substitutable positions. When the number of substituents is 2 or more, the respective substituents may be the same or different.

In the "aromatic heterocyclic group which may optionally have a substituent(s)" as represented by R, the "aromatic heterocyclic group" includes, for example, a monovalent group formed by removing one hydrogen atom from a 5- to 14-membered (preferably 5- to 10-membered) aromatic hetero-ring containing 1 to 4 hetero atoms of one or two species selected from a nitrogen atom, a sulfur atom and an oxygen atom, in addition to the carbon atoms. Examples of the "5- to 14-membered (preferably 5- to 10-membered) aromatic hetero-ring" include aromatic hetero-rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, etc.; and rings formed by condensing any one of these rings (preferably monocycle) with one or more (preferably one or two) aromatic rings (e.g., benzene ring, etc.).

Examples of the "aromatic heterocyclic group" include thienyl (e.g., 2-thienyl, 3-thienyl), furyl (e.g., 2-furyl, 3-furyl), pyridyl (e.g., 2-pyridyl, 3-pyridyl, 4-pyridyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 3-pyrrolyl), imidazolyl (e.g., 2-imidazolyl), pyridazinyl (e.g., 3-pyridazinyl), isothiazolyl (e.g., 3-isothiazolyl), isoxazolyl (e.g., 3-isoxazolyl), indolyl (e.g., 1-indolyl, 2-indolyl, 3-indolyl), benzothiazolyl (e.g., 2-benzothiazolyl), benzothienyl (e.g., 2-benzo[b]thienyl, 3-benzo[b]thienyl), benzofuranyl (e.g., 2-benzo[b]furanyl, 3-benzo[b]furanyl), etc. Among them, a 5- to 6-membered heterocyclic group containing 1 to 3 hetero atoms selected from a nitrogen atom, a sulfur atom and an oxygen atom in addition to the carbon atoms (e.g., a pyridyl such as 2-pyridyl, 3-pyridyl, 4-pyridyl) is preferred.

In the "aromatic heterocyclic group which may optionally have a substituent(s)" as represented by R, examples of the "substituent(s)" include the same substituents described above in the "hydrocarbon group which may optionally have a substituent(s)" with the same number of substituents. Among them, hydroxy or the like is preferred.

Examples of the "amino group which may optionally have a substituent(s)" as represented by R include amino, guanidino, an amino having a substituent(s), guanidino having a substituent(s), etc.

In the "amino having a substituent(s)" and "guanidino having a substituent(s)", the "substituent(s)" includes, for example, the "hydrocarbon group which may optionally have a substituent(s)" as represented by R, etc.

Preferred examples of R are benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, guanidino, etc.

Furthermore, the compounds represented by the formula (I) can be present as tautomers, which are represented by the following the formulas, or as salts thereof:

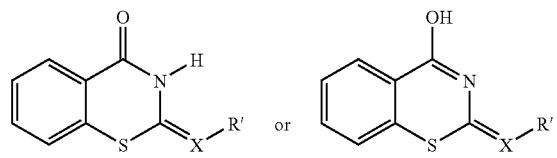

wherein X represents CH or a nitrogen atom, and R' represents a group formed by removing X—H from R. The compounds represented by the formula (I) or salts thereof (hereinafter sometimes briefly referred to as Compound (I)) include the tautomers, salts thereof, and a mixture thereof with Compound (I).

The "salts" of compounds represented by the formula (I) and tautomers thereof are preferably pharmaceutically acceptable salts, which include, for example, salts with inorganic bases, salts with organic bases, salts with inorganic acids, salts with organic acids, salt with basic or acidic amino acids, and so on. Preferred examples of the salts with inorganic bases include alkali metal salts such as sodium salts, potassium salts; alkaline earth metal salts such as calcium salts, magnesium salts; aluminum salts, ammonium salts, and the like. Preferred examples of the salts with organic bases include trimethylamine salts, triethylamine salts, pyridine salts, picoline salts, ethanolamine salts, diethanolamine salts, triethanolamine salts, dicyclohexylamine salts, N,N'-dibenzylethylenediamine salts, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc. Preferred examples of the salts with acidic amino acids include salts with aspartic acid, glutamic acid, etc.

Specific examples of Compound (I) include the compounds in REFERENCE EXAMPLES 1 through 5, which will be later described.

Compound (I) may be commercially purchased, or may be manufactured according to well-known methods or those with modifications.

Examples of the metalloporphyrins of (c) described above include hemin, hematin, Sn (IV) protoporphyrin IX, Zn (II) protoporphyrin IX, Co (III) protoporphyrin IX, etc.

The substance capable of binding to MIF has excellent cell death inhibitory activities. The substance inhibits, for example, cell death induced by oxidative stress, cell death induced by serum depletion, cell death induced by deficiency of growth factors, cell death induced by HMG-CoA reductase inhibitors, cell death induced by anticancer agents, cell death induced by NO, cell death induced by amyloid β protein, etc.

In addition, the substance capable of binding to MIF has an activity of promoting the expression of genes under control of Antioxidant response element (ARE) (e.g., genes of factors for protecting cells from various stresses; etc.), an activity of enhancing (promoting) the production of gene proteins (gene products) under control of ARE, or an activity of promoting their activities; and the like.

As the genes under control of ARE, there are Heme oxygenase-1, Liver glutathione S-transferase Ya subunit, Liver glutathione S-transferase Yc subunit, Glutathione S-transferase Yb subunit, Glutathione S-transferase Yc1 subunit, Gamma-glutamylcysteine synthetase, NAD(P)H: quinone reductase, UDP-glucuronosyltransferase, exon 1, Bilirunin-specific UDP-glucuronosyltransferase, or NAD(P)H-menadione oxidereductase, etc.

As such, the compound capable of binding to MIF increases the factors for protecting cells from stress, thereby to strongly inhibit cell death induced by various causes.

The substance capable of binding to MIF is low toxic and is thus useful as a cell death inhibitor for prevention and treatment of, e.g., heart diseases (e.g., myocardiopathy, heart failure, angina pectoris, myocardial infarction, etc.), neurodegenerative diseases (e.g., Parkinson's disease, Alzheimer's disease, triplet repeat disease, prion disease, amyotrophic lateral sclerosis, cerebellar degeneration, retinitis pigmentosa, etc.), cerebrovascular diseases (e.g., cerebral infarction, etc.), central nervous infections (e.g., HIV encephalitis, bacterial meningitis, etc.), traumatic diseases (e.g., spinal cord injury, brain injury, etc.), demyelinating diseases (e.g., multiple sclerosis, etc.), bone/joint diseases (e.g., osteoporosis, arthritis deformans, rheumatism, etc.), kidney diseases (e.g., ischemic acute renal failure, hemolytic uremic syndrome, acute tubular necrosis, hydronephrosis, glomerulonephritis, diabetic nephropathy, etc.), liver diseases (e.g., viral hepatitis, alcoholic hepatitis, etc.), myelodysplastic diseases (e.g., aplastic anemia, etc.), arteriosclerosis, diabetes, pulmonary hypertension, sepsis, inflammatory bowel diseases, autoimmune diseases (e.g., systemic lupus erythematosus, atopic dermatitis, etc.), failure accompanying rejection in organ transplantation, AIDS, cancers (e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.), as a protecting agent for transplant organs, etc.

The substance capable of binding to MIF is prepared into a pharmaceutical composition according to publicly known methods, and the composition can be safely administered to mammals (e.g., human, monkey, etc.) orally or parenterally in the form of various preparations.

Specifically, the substance capable of binding to MIF is mixed with pharmaceutically acceptable carriers and administered orally in the form of tablets, pills, granules, capsules, syrups, emulsions, suspensions, etc. or parenterally, i.e., intravenously, subcutaneously or intramuscularly, in the form of injections, suppositories, buccals or the like. The substance may be administered sublingually, subcutaneously, intramuscularly, etc., in the form of sustained-release preparations such as buccals, microcapsules, etc.

The pharmaceutically acceptable carriers described above include a wide variety of organic or inorganic carrier materials conventionally used for pharmaceutical preparations, and are mixed, for example, as excipients, lubricants, binders, disintegrators, solvents, solubilizers, suspending agents, isotonizing agents, buffers, soothing agents, etc. If necessary, additives such as preservatives, antioxidants, coloring agents, sweeteners, etc. can also be used.

Preferred examples of the excipients described above include lactose, white sugar, D-mannitol, starch, crystalline cellulose, light silicic anhydride, etc. Preferred examples of the above-mentioned lubricants include magnesium stearate, calcium stearate, talc, colloidal silica, etc. Preferred examples of the binders described above include crystalline cellulose, white sugar, D-mannitol, dextrin, hydroxypropyl cellulose, hydroxypropylmethyl cellulose, polyvinyl pyrrolidone, etc. Preferred examples of the disintegrators described above include starch, carboxymethyl cellulose, calcium carboxymethyl cellulose, sodium croscarmellose, sodium carboxymethyl starch, etc. Preferred examples of the solvents described above include water for injection, alcohol, propylene glycol, Macrogol, sesame oil, corn oil, etc. Preferred examples of the solubilizers described above include polyethylene glycol, propylene glycol, D-mannitol, benzyl benzoate, ethanol, trisaminomethane, cholesterol, triethanolamine, sodium carbonate, sodium citrate, etc. Preferred examples of the suspending agents described above include surfactants such as stearyl triethanolamine, sodium laurylsulfate, lauryl aminopropionate, lecithin, benzalkonium chloride, benzetonium chloride, glycerine monostearate, etc.; hydrophilic polymers such as polyvinyl alcohol, polyvinyl pyrrolidone, sodium carboxymethyl cellulose, methyl cellulose, hydroxymethyl cellulose, hydroxyethyl cellulose, hydroxypropyl cellulose, etc. Preferred examples of the isotonizing agents described above include sodium chloride, glycerine, D-mannitol, etc. Preferred examples of the buffers described above include buffers of phosphates, acetates, carbonates, citrates, etc. Preferred examples of the soothing agents described above include benzyl alcohol, etc. Preferred examples of the preservatives described above include para-oxybenzoic acid esters, chlorobutanol, benzyl alcohol, phenethyl alcohol, dehydroacetic acid, sorbic acid, etc. Preferred examples of the antioxidants described above include sulfites, ascorbic acid, etc.

The dose of the substance capable of binding to MIF varies depending on pathological conditions; age, sex and weight of the subject to be administered; timing and interval of administration, nature, formulation and type of the pharmaceutical composition; kinds of active ingredients; etc. For the treatment of heart diseases, the daily dose for an adult is usually, but not particularly limited to, about 10 µg to about 100 mg/kg body weight, preferably 100 µg to 50 mg/kg body weight. The daily dose is usually divided and administered 1 to 4 times per day.

The substance capable of binding to MIF is contained in the cell death inhibitor in an amount of about 0.01 to 100% by weight based on the total weight of the inhibitor.

When the cell death inhibitor of the present invention is used in combination with HMG-CoA reductase inhibitors (e.g., Simvastatin, Atorvastatin, etc.), fibrate-type antihyperlipidemic drugs (e.g., Gemfibrozil, etc.), anticancer agents (e.g., Ifosfamide, UFT, Adriamycin, Doxorubicin, Peplomycin, Cisplatin, Cyclophosphamide, 5-FU, Methotrexate, Mitomycin C, Mitoxantrone, etc.) or the like, side effects by HMG-CoA reductase inhibitors, fibrate-type antihyperlipidemic drugs, anticancer agents, etc., which give damages to normal cells, are alleviated.

The cell death inhibitor can be screened using MIF.

The compound binding to MIF inhibits cell death of various cells and thus, the substance having a cell death inhibitory activity can be obtained by screening the substance that binds to MIF. Preferably, the substance having the cell death inhibitory activity includes a substance, which promotes the expression of genes under control of ARE or the like.

Specific examples of the screening method of the present invention include a method of screening the substance which binds to MIF, utilizing surface plasmon sensor technique; and so on. Specifically, MIF is immobilized on the surface of BIAcore 3000 sensor chips, and then a solution of test compound dissolved in phosphate-buffered saline (PBS), etc. is applied onto the chip surface. By monitoring the change in surface plasmon, the substance binding to MIF is screened. For example, the test compound, which gives the measuring value of 5 resonance units or more for the change in surface plasmon, is selected as the cell death inhibitor.

The test compounds include, for example, peptides, proteins, non-peptide compounds, synthetic compounds, fermentation products, cell extracts, plant extracts, animal tissue extracts, etc. These compounds may be novel or publicly known compounds.

A specific example of the screening method of the present invention includes a method of screening the substance binding to MIF, in which (i) when MIF is mixed with a labeled compound capable of binding to MIF (labeled compound) and (ii) when a test compound and MIF are mixed with a labeled compound capable of binding to MIF (labeled compound), the binding amounts of the labeled compounds bound to the macrophage migration inhibitory factor are measured, respectively, and comparison is made therebetween.

As the compounds for the labeled compounds, Compound (I), metalloporphyrins, the compounds described in WO 03/020719 and salts thereof, etc. are employed.

The labeling agents used for labeling include, for example, radioactive isotopes, enzymes, fluorescent substances, luminescent substances, lanthanide elements, spin reagents, etc. For the radioisotopes, for example, [$^{125}$I], [$^{131}$I], [$^{3}$H], [$^{14}$C], [$^{32}$P], [$^{33}$P], [$^{35}$S], [$^{59}$Fe], and the like are employed. As the enzymes described above, stable enzymes with high specific activity are preferred; for example, β-galactosidase, β-glucosidase, alkaline phosphatase, peroxidase, malate dehydrogenase, and the like are used. Examples of the fluorescent substances used are cyanine fluorescent dyes (e.g., Cy2, Cy3, Cy5, Cy5.5, Cy7 (manufactured by Amersham Bioscience), etc.), fluorescamine, fluorescein isothiocyanate, and the like. For the luminescent substances, for example, luminol, luminol derivatives, luciferin, lucigenin, etc. are used.

When a test compound inhibits at least about 20%, preferably at least 30%, and more preferably at least about 50% of the binding amount of the labeled compound bound to MIF in the case of (i) described above, the test compound is selected to be a substance binding to MIF (cell death inhibitor).

The test compounds include, for example, peptides, proteins, non-peptide compounds, synthetic compounds, fermentation products, cell extracts, plant extracts, animal tissue extracts, etc. These compounds may be novel or publicly known compounds.

The screening kit of the present invention comprises MIF and the labeled compounds described above, if necessary.

The compounds or salts thereof, which are obtained using the screening method or screening kit of the present invention, are compounds having the cell death inhibitory activity or salts thereof, and are used similarly as the cell death inhibitors described above.

In the specification and drawings, the codes of bases, amino acids and the like are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
NO: nitrogen monoxide Substituents, protecting groups and reagents frequently used in this specification are presented as the codes below.

Me: methyl group
Et: ethyl group
Bu: butyl group
Ph: phenyl group
TC: thiazolidine-4(R)-carboxamido group
Tos: p-toluenesulfonyl
CHO: formyl
Bzl: benzyl
Cl$_2$-Bzl: 2,6-dichlorobenzyl
Bom: benzyloxymethyl
Z: benzyloxycarbonyl
Cl—Z: 2-chlorobenzyloxycarbonyl
Br—Z: 2-bromobenzyloxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxylmide
DCC: N,N'-dicyclohexylcarbodiimide The sequence identification numbers in the sequence listing of the specification indicate the following sequences, respectively.

[SEQ ID NO: 1]

This shows the base sequence of a sense strand, which coincides with the N terminus of rat MIF used in EXAMPLE 1, containing the NdeI cleavage site at the 5' end.

[SEQ ID NO: 2]

This shows the base sequence of an anti-sense strand, which coincides with the C terminus of rat MIF used in EXAMPLE 1, containing the SapI cleavage site at the 5' end.

[SEQ ID NO: 3]

This shows the base sequence of a sense strand, which coincides with the N terminus of mouse MIF used in EXAMPLE 1, containing the NdeI cleavage site at the 5' end.

[SEQ ID NO: 4]

This shows the base sequence of an anti-sense strand, which coincides with the C terminus of mouse MIF used in EXAMPLE 1, containing the SapI cleavage site at the 5' end.

The hybridoma BWS48-1 obtained in REFERENCE EXAMPLE 7 later described has been on deposit since Mar. 28, 2002 under the Accession Number FERM BP-7991 at the National Institute of Advanced Industrial Science and Technology, International Patent Organism Depositary, located at Central 6, 1-1-1 Higashi, Tsukuba, Ibaraki, Japan (postal code 305-8566).

Hereinafter, the present invention is described in more detail with reference to REFERENCE EXAMPLES, EXPERIMENTAL EXAMPLES and EXAMPLES, but these are not deemed to limit the scope of the present invention.

In REFERENCE EXAMPLES below, "%" means percent by weight, unless otherwise indicated.

The $^1$H-NMR spectra were measured with a Varian GEMINI 200 (200 MHz) model spectrometer using tetramethylsilane as an internal standard. All δ values are shown in terms of ppm.

Other abbreviations in the specification are used to mean the following.

s: singlet
d: doublet
dd: double doublet
t: triplet
q: quartet
m: multiplet
J: coupling constant
Hz: Hertz
CDCl$_3$: heavy chloroform
$^1$H-NMR: proton nuclear magnetic resonance
IR: infrared absorption spectrum Reference Example 1

2-(2-Pyridyl)-4H-1,3-benzothiazin-4-one (Compound 1)

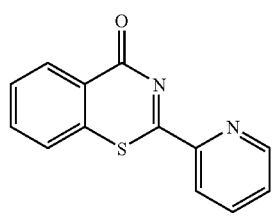

Methyl thiosalicylate (1.6 g, 9.51 mM) and 2-cyanopyridine (1.0 g, 9.60 mM) were dissolved in toluene (2 ml), and triethylamine (2 ml, 14.4 mM) was added to the solution. After heating for 8 hours under reflux, toluene was removed by distillation. Ethanol was added to the residue and the precipitates were taken out by filtration to give crude crystals (1.7 g). The crude crystals were purified by silica gel column chromatography (hexane:chloroform=5:1→chloroform) to give the title compound as crystals (1.0 g, 43.4%).

Elemental analysis as $C_{13}H_8N_2OS$

Calcd. (%) C, 64.98; H, 3.36, N, 11.66.

Found (%) C, 64.93; H, 3.31, N, 11.59.

$^1$H-NMR (CDCl$_3$) δ: 7.50-7.75 (m, 4H), 7.85-8.00 (m, 1H), 8.50-8.60 (m, 2H), 8.70-8.80 (m, 1H).

IR (KBr): 1660 cm$^{-1}$

Reference Example 2

2-(3-Pyridyl)-4H-1,3-benzothiazin-4-one

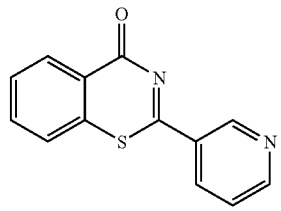

Methyl thiosalicylate (1.8 g, 10.7 mM) and 3-cyanopyridine (1.1 g, 10.56 mM) were dissolved in toluene (5 ml), and triethylamine (2 ml, 14.4 mM) was added to the solution. After heating for 48 hours under reflux, the same procedures as in REFERENCE EXAMPLE 1 were carried out to give the title compound as crystals (1.1 g, 43.4%).

Elemental analysis as $C_{13}H_8N_2OS$

Calcd. (%) C, 64.98; H, 3.36, N, 11.66.

Found (%) C, 64.97; H, 3.33, N, 11.63.

Reference Example 3

2-(4-Pyridyl)-4H-1,3-benzothiazin-4-one

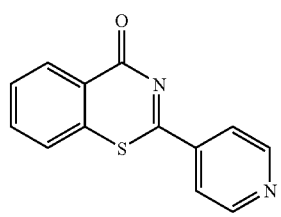

Methyl thiosalicylate (2.0 g, 11.9 mM) and 4-cyanopyridine (1.2 g, 11.5 mM) were dissolved in toluene (5 ml), and triethylamine (2 ml) was added to the solution. After heating for 22 hours under reflux, the same procedures as in REFERENCE EXAMPLE 1 were carried out to give the title compound as crystals (850 mg, 30.7%).

Elemental analysis as $C_{13}H_8N_2OS$

Calcd. (%) C, 64.98; H, 3.36, N, 11.66.

Found (%) C, 65.07; H, 3.15, N, 11.62.

Reference Example 4

Ethyl 2-(4-oxo-3,4-dihydro-2H-1,3-benzothiazin-2-ylidene)acetate

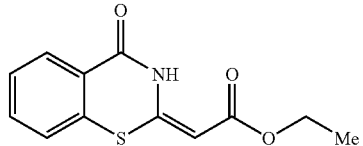

Methyl thiosalicylate (6 g, 35.7 mM) and ethyl cyanoacetate (4 g, 35.4 mM) were dissolved in toluene (10 ml), and triethylamine (5 ml, 35.8 mM) was added to the solution, followed by heating for 7 hours under reflux. After the reaction solution was concentrated, ethanol was added to the residue. The mixture was allowed to stand, and the crystals precipitated were taken out by filtration to give crude crystals. The crude crystals were recrystallized from ethanol to give the title compound as needles (5.4 g, 60.7%).

Elemental analysis as $C_{12}H_{11}NO_3S$
Calcd. (%) C, 57.82; H, 4.45, N, 5.62.
Found (%) C, 57.86; H, 4.36, N, 5.51.
$^1$H-NMR (CDCl$_3$) δ: 1.31 (t, 3H, J=7.0 Hz), 4.22 (q, 2H, J=7.0 Hz), 5.57 (s, 1H), 7.35 (t, 2H, J=7.4 Hz), 7.50-7.60 (m, 1H), 8.28 (d, 1H, J=7.4 Hz), 9.73 (s, 1H).
IR (KBr) cm$^{-1}$: 1660, 1590, 1580, 1560, 1440, 1295, 1165, 730.

Reference Example 5

2-[2-Oxo-2-(1-piperidinyl)ethylidene]-2,3-dihydro-4H-1,3-benzothiazin-4-one

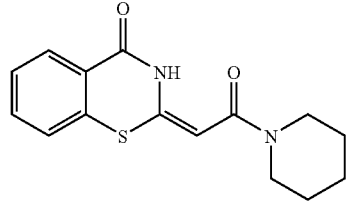

Methyl thiosalicylate (1.7 g, 10.1 mM) and 1-cyanoacetylpiperidine (2.0 g, 13.1 mM) were dissolved in toluene (5 ml), and triethylamine (2 ml, 14.4 mM) was added to the solution. After heating for 30 hours under reflux, the reaction solution was concentrated to give crude crystals. The crude crystals were recrystallized from ethanol to give the title compound as needles (730 mg, 25%).

Elemental analysis as $C_{15}H_{16}N_2O_2S$
Calcd. (%) C, 62.48; H, 5.59, N, 9.71.
Found (%) C, 62.22; H, 5.58, N, 9.65.
NMR (CDCl$_3$) δ: 1.30-1.80 (m, 6H), 3.30-3.70 (m, 4H), 5.30 (s, 1H), 6.90-7.60 (m, 3H), 8.27 (dd, 1H, J=8 Hz, J=2 Hz).
IR (KBr) cm$^{-1}$: 1660, 1595, 1560.

Reference Example 6

Preparation of Rat MIF Protein and Mouse MIF Protein (1) Construction of MIF Expression Vectors After T7 promoter expression plasmid pET32b (+) (Novagen, Inc.) was cleaved with SapI and TthIII, the cleaved site was blunt ended and then recyclized to give pET32b-1 deprived of the SapI cleavage site from pET32b (+). Next, pCYB1 (IMPACT I: One-Srep Protein Purification System, New England BioLabs, Inc.) was cleaved with NdeI and BglI, and DNA fragments in the region encoding the multiple cloning site and the intein-chitin binding domain fusion protein were recovered. This BglI cleavage site was blunt ended and then inserted between the NdeI and EcoRV sites of pET32b-1 to give pET32b-Int-CBD.

Next, the region encoding MIF was amplified from the complementary DNA (cDNA) library of rat and mouse brains (GIBCO BRL, Inc.) by polymerase chain reaction (PCR). For the cDNA amplification of rat MIF, a sense strand (SEQ ID NO: 1) which coincided with the N terminus of rat MIF containing the NdeI cleavage site at the 5' end and an antisense strand (SEQ ID NO: 2) which coincided with the C terminus of rat MIF containing the SapI cleavage site at the 5' end were used. For the cDNA amplification of mouse MIF, a sense strand (SEQ ID NO: 3) which coincided with the N terminus of mouse MIF containing the NdeI cleavage site at the 5' end and an antisense strand (SEQ ID NO: 4) which coincided with the C terminus of mouse MIF containing the SapI cleavage site at the 5' end were used. After the amplified MIFcDNA was cleaved with NdeI and SapI, the cleavage products were inserted between the NdeI cleavage site and the SapI cleavage site of pET32b-Int-CBD to give MIF-intein-chitin binding domain fusion protein expression plasmids pET32b-rMIF-Int-CBD and pET32b-mMIF-Int-CBD, respectively. The MIFcDNA sequences in the expression plasmids obtained were confirmed using DNA Sequence System (Applied Biosystems, Inc.).

(2) Preparation of Rat MIF Protein

After pET32b-rMIF-Int-CBD was transfected to *Escherichia coli* BL21 (DE3) (Novagen), the cells were plated on ampicillin-supplemented LB medium (1% tryptone, 0.5% yeast extract, 0.5% NaCl) (LBamp medium), followed by incubation while shaking at 37° C. overnight. The cells were transferred to LBamp medium in a density of 1%, followed by incubation while shaking at 37° C. for about 2 hours and then incubation at 22° C. for about an hour. After 0.4 mM of isopropyl-1-thio-β-D-galactopyranoside (IPTG) was added thereto, incubation was continued at 15° C. for further 24 hours to induce the expression of rat MIF-intein-chitin binding domain fusion protein. After completion of the incubation, *Escherichia coli* was recovered and suspended in a column buffer (20 mM Tris-HCl; pH 8.0, 500 mM NaCl, 0.1 mM EDTA) containing 1/10 volume of 0.1% Triton X-100, followed by ultrasonication. The cell lysate was centrifuged at 4° C. and 12000 rpm for 30 minutes to recover the supernatant. The recovered supernatant was passed through a chitin bead column (New England Biolabs), which had been equilibrated with the column buffer containing 0.1% Triton X-100 so that the MIF-intein-chitin binding domain fusion protein was allowed to bind to the column. Thereafter, the column was washed with the 0.1% Triton X-100-containing column buffer in a volume of 10 times the column size and the column buffer in a volume of 10 times the column size to remove non-specifically bound proteins and accompanied substances. Next, the buffer within the column was replaced with the column buffer containing 50 mM dithiothreitol. The column was allowed to stand at 4° C. for at least 16 hours, thereby to excise the MIF protein from the fusion protein, utilizing the protein splicing activity of intein. The excised MIF protein was eluted by the column buffer, followed by dialysis to 20 mM sodium phosphate buffer.

(3) Preparation of Mouse MIF Protein

Mouse MIF protein was obtained by almost the same procedures as in rat MIF protein, except that 0.1% Triton X-100 was not added to the column buffer (20 mM Tris-HCl; pH 8.0, 500 mM NaCl, 0.1 mM EDTA) used for suspension when the *Escherichia coli* expressing protein was ultrasonicated.

Reference Example 7

Production of Monoclonal Anti-Mouse MIF Antibody (1) Preparation of Anti-Mouse MIF-Producing Hybridoma
(i) Immunization BALB/C female mice of 6 to 8 weeks old were immunized subcutaneously with mouse MIF obtained in REFERENCE EXAMPLE 6 in about 50 μg/mouse with complete Freund's adjuvant. Subsequently, the animal was boostered 2 or 3 times with the same volume of the immunogen with incomplete Freund's adjuvant every two other weeks.
(ii) Measurement of Antibody Titer in Sera from Mice Immunized with Mouse MIF The animal was boostered twice with mouse MIF every two other weeks, and one week later, blood was withdrawn from the ocular fundus. After the blood was further centrifuged at 4° C. and 12,000 rpm for 15 minutes, the supernatant was recovered to give antisera. The antibody titer in antisera was determined by the method described below. In order to prepare mouse MIF-bound microplate, 100 μl each of phosphate buffered saline (PBS, pH 7.4) containing 2 μg/ml of mouse MIF was dispensed onto a 96-well microplate, which was allowed to stand at 4° C. for 24 hours. Next, the plate was washed with PBS containing 0.5% Tween-20. To block redundant binding sites in the well, a 200 μl aliquot of PBS containing 2% BSA (manufactured by SIGMA, Inc.) was dispensed, followed by treating at 37° C. for an hour.

To each well of the anti-mouse MIF-bound microplate obtained, 100 μl of antisera diluted with PBS was added. The mixture was reacted at room temperature for 2 hours. Next, after the plate was washed with PBS containing 0.5% Tween-20, 100 μl of HRP-labeled anti-mouse IgG-gamma (diluted 5,000-fold with PBS) was added thereto followed by reacting them at room temperature for an hour. After the plate was washed with PBS containing 0.5% Tween-20, 100 μl of TMB Microwell peroxidase substrate system (KIRKEGAARD & PERRY LAB, INC., available from Funakoshi Pharmaceutical Co., Ltd.), was added to the enzyme activity on the solid phase and was then allowed to stand at room temperature for 10 minutes. By adding 100 μl of 1M phosphoric acid, the reaction was terminated and the absorption at 450 nm was read on a plate reader (BICHROMATIC, manufactured by Dainippon Pharmaceutical Co., Ltd.).
(iii) Production of Monoclonal Anti-Mouse MIF Antibody Mice showing relatively high antibody titers received final immunization by intravenous injection with solutions of 10 to 100 μg of the immunogen in 0.2 ml of saline. After 4 days of the final immunization, the spleen was removed from mice, and spleen cells were emigrated on slide glasses and filtered through a mesh. The cells were suspended in Eagles' minimum essential medium (MEM) to give the spleen cell suspension. BALB/C mouse-derived myeloma cells P3-X63.Ag8.U1 (P3U1) were used as cells for cell fusion (Current Topics in Microbiology and Immunology, 81, 1, 1978).

The cell fusion was performed by modifications of the original method (Nature, 256, 495, 1975). That is, the spleen cells and P3U1 were washed 3 times with serum-free MEM, respectively, and mixed in a 5:1 ratio in terms of the count of the spleen cells to P3U1. The mixture was centrifuged at 800 rpm for 15 minutes to precipitate the cells. After the supernatant was thoroughly removed, the precipitates were lightly loosened and 0.3 ml of 45% polyethylene glycol (PEG) 1500 (manufactured by Sigma Inc.) was added thereto. The mixture was settled for 7 minutes on a warm water bath at 37° C. to effect fusion. After the fusion, MEM was added to the cells at a rate of 2 ml/min to reach 15 ml of MEM in total. Thereafter, the mixture was centrifuged at 600 rpm for 15 minutes to remove the supernatant. The cell precipitates were suspended in CM-B medium (Sanko Junyaku Co., Ltd.) to contain $2 \times 10^5$ of P3U1 per ml, and the suspension was seeded on 192 wells of a 24-well Multidish plates (manufactured by Costar, Inc.) in 1 ml well. After seeding, the cells were incubated at 37° C. in a 5% carbon dioxide gas incubator. After 24 hours, 1 ml each/well of CM-B medium containing HAT ($1 \times 10^{-4}$ M hypoxanthine, $4 \times 10^{-7}$ M aminopterin and $1.6 \times 10^{-3}$ M thymidine) (HAT medium) was added thereto to initiate the HAT selection culture. The HAT selection culture was continued by discarding 1 ml of the old medium on days 3, 5, 7 and 9 after initiation of the culture and then replenishing 1 ml of HAT medium. Growth of the hybridoma was noted on 9 to 14 days after the cell fusion. When the medium turned yellow (ca. $1 \times 10^6$ cells/ml), the antibody titer was determined in accordance with the method described in (ii). Then, the cells were cloned to acquire hybridoma BWS48-1.

Mice (BALB/C) previously administered intraperitoneally with 0.5 ml of mineral oil were administered intraperitoneally with this hybridoma in $1 \times 10^6$ cells/mouse. Then, the ascites containing the antibody was collected 6 to 20 days after.

The monoclonal antibody named BWS48-1a was purified from the obtainedascites, using a protein-G column. That is, 6 to 20 ml of the ascites was diluted in a doubled volume of binding buffer [20 mM phosphate buffer (pH 7.0)] and the dilution was passed through a Recombinant Protein-G Sepharose (manufactured by Pharmacia) column, which had been previously equilibrated with the binding buffer, and the specific antibody was eluted with an eluting buffer [0.1 M glycine buffer (pH 2.7)]. The eluate was dialyzed to PBS at 4° C. for 2 days. The dialysate was subjected to bacteria-free filtration through a 0.22 μm filter (manufactured by Millipore Inc.), which was stored at 4° C. or −80° C.

Experimental Example 1

Binding of MIF to Compound 1

The binding of rat MIF obtained in REFERENCE EXAMPLE 6 to Compound 1 obtained in REFERENCE EXAMPLE 1 was analyzed using BIACORE 3000 (manufactured by Biacore).

Rat MIF was immobilized on a sensor chip CM5 (manufactured by Biacore). Then, phosphate buffered saline (PBS) containing 10 μM of Compound 1 was flown over the sensor chip and changes in the surface plasmon resonance signal were monitored as the binding of the compound to rat MIF.

The results are shown in FIG. 1.

From the results it is understood that Compound 1 binds to MIF.

Experimental Example 2

(1) Myocardial Cell Death Inhibitory Activity of the Monoclonal Antibody BWS48-1a and Compound 1

Neonates (within one day after birth) were obtained from pregnant Wistar rats purchased from Charles River Japan, Inc. and anesthetized with ether. After sterilization with 70% ethanol, the heart was removed with forceps. After washing with phosphate buffered saline (manufactured by Takara Co., Ltd., T900), the heart removed was minced with surgical scissors. The pieces of tissue were washed 4 or 5 times with phosphate buffered saline to remove most of non-cardiomyocytes derived from blood. To the pieces of tissue corresponding to 10 neonates, 5 ml of an enzyme solution [which is a solution of trypsin (1.25 mg) (manufactured by Difco) and collagenase (0.25 mg) (manufactured by Sigma) in phosphate buffer (1 ml)] was added. The mixture was stirred for 15 minutes with a stirrer while maintaining at 37° C. After 2.5 ml of the enzyme solution was replenished, the mixture was stirred for further 15 minutes, and this procedure was repeated twice. Subsequently, Medium 199 (manufactured by Gibco) containing 10% fetal cow serum (manufactured Biowicker, Inc.) was added to the mixture in a half volume of the enzyme solution to terminate the enzymatic reaction. After filtering through a cell strainer (manufactured by Falcon), the mixture was centrifuged at 400×g for 5 minutes to collect the cells.

The thus collected cells corresponding to 10 neonates were suspended in 50 ml of Medium 199 containing 10% fetal cow serum, and 10 ml each of the suspension was seeded on a 100 mm Petri dish (manufactured by Iwaki Co., Ltd.), followed by incubation for an hour in a $CO_2$ incubator set at 37° C. and 5% $CO_2$. The cells were then recovered, filtered through a cell strainer and centrifuged at 400×g for 5 minutes to collect primary cardiomyocytes derived from rat neonates.

Next, the primary cardiomyocytes derived from rat neonates (corresponding 10 neonates) were suspended in 2 ml of a hypotonic solution [solution obtained by dissolving $NH_4Cl$ (8.29 g), $KHCO_3$ (1.0 g) and EDTA/2Na (ethylenediaminetetraacetic acid disodium; manufactured by Dojin Chemical Laboratory) (37 mg) in water (1 L)]. The suspension was allowed to stand for 3 minutes to disrupt erythrocytes. To the suspension 10 ml of Medium 199 containing 10% fetal cow serum was added, and the mixture was centrifuged at 400×g for 5 minutes to collect the primary cardiomyocytes derived from rat neonates. The cells were suspended in Medium 199 containing 10% fetal cow serum and the suspension was filtered through a cell strainer. An aliquot of the cardiomyocytes suspension obtained was taken out and 0.3% trypan blue was added thereto. The mixture was gently stirred and the count of cardiomyocytes was counted with a hemocytometer.

The primary cardiomyocytes derived from rat neonates thus prepared were suspended in Medium 199 containing 10% fetal cow serum in $3 \times 10^5$ cells/ml, and the suspension was seeded on a 96-well plate in 0.1 ml well, followed by incubation for a day in a $CO_2$ incubator set at 37° C. and 5% $CO_2$. After stirring with a micromixer (manufactured by Taiyo Kagaku Kogyo Co., Ltd.), the medium was replaced 3 times with serum-free Medium 199 to remove serum, and a sample to be tested was added thereto. Incubation was continued for further 4 days to induce cell death. As the sample to be tested, the monoclonal antibody BWS48-1a obtained in REFERENCE EXAMPLE 7 or Compound 1 obtained in REFERENCE EXAMPLE 1 was used.

Thereafter, fetal cow serum was added thereto to reach 10%. After further incubation in a $CO_2$ incubator set at 37° C. and 5% $CO_2$ for about 17 hours, the viable cell count was determined using a cell count assay kit (manufactured by Dojin Chemical Laboratory) in which WST-8 [2-(2-methoxy-4-nitrophenyl)-3(4-nitrophenyl)-5-(2,4-disulfophenyl)-2H-tetrazolium, monosodium salt] was used as a chromogen, thereby to examine the myocardial cell death inhibitory activity.

The experiment described above was carried out independently in 3 runs.

Figure 2:
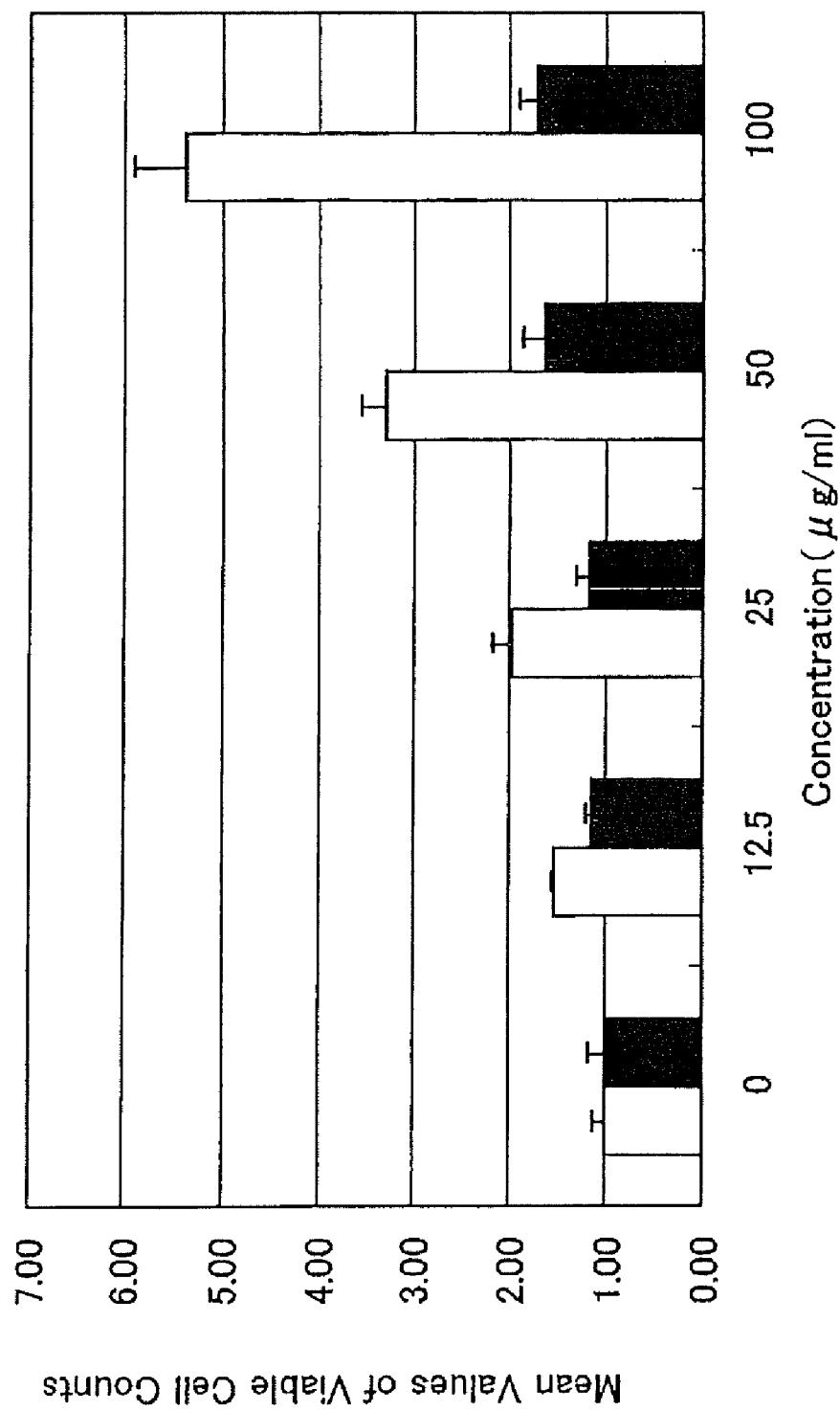
FIG. 2 shows the myocardial cell death inhibitory effects of monoclonal antibody BWS48-1a, wherein hollow rectangle and solid rectangle represent BWS48-1a and control antibody, respectively.

When the viable cell count in the group with no antibody added was made 1, mean values (±SD) of the viable cell counts in the group with control antibody (mouse IgG) added and the groups with the monoclonal antibody BWS48-1a added in various concentrations are shown in FIG. 2.

The mean value (±SD) in the minimum effective concentration of Compound 1 required for inhibiting the cell death was 0.015±0.011 μM. The concentration of Compound 1 required for increasing the mean cell count by 30% when compared to the cell count without the addition of Compound 1 was determined to be the minimum effective concentration.

From the foregoing results, it is noted that the monoclonal antibody BWS48-1a and Compound 1 exhibit the activity of inhibiting myocardial cell death.

(2) Myocardial Cell Death Inhibitory Activity of Hemin aAnd Hematin

The primary cardiomyocytes derived from rat neonates prepared as described in (1) above were suspended in Medium 199 containing 10% fetal cow serum in $3 \times 10^5$ cells/ml, and the suspension was seeded on a 96-well plate by 0.1 ml each/well, followed by incubation for a day in a $CO_2$ incubator set at 37° C. and 5% $CO_2$. After stiffing with a micromixer (manufactured by Taiyo Kagaku Kogyo Co., Ltd.), the medium was replaced 3 times with serum-free Medium 199 to remove serum, and a sample to be tested was added thereto. Incubation was continued for further 4 days to induce cell death. As the sample to be tested, hemin or hematin was used.

Subsequently, fetal cow serum was added thereto to become 10%. After further incubation in a $CO_2$ incubator set at 37° C. and 5% $CO_2$ for about 17 hours, the viable cell count was determined using a cell count assay kit (manufactured by Dojin Chemical Laboratory) in which WST-8 was used as a chromogen. Thus, the myocardial cell death inhibitory activity was examined.

The experiment described above was carried out independently in 3 runs.

Figure 7:
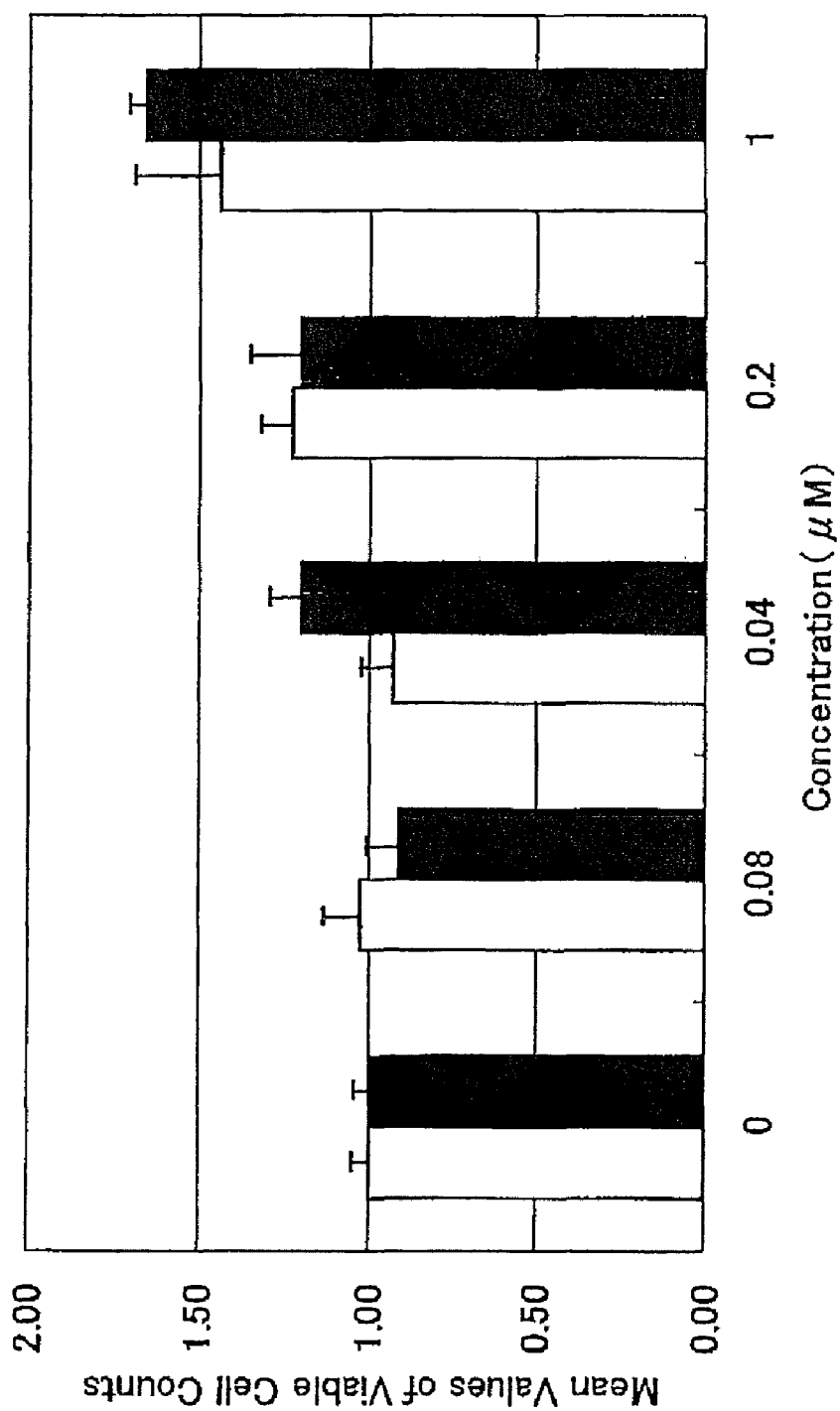
FIG. 7 shows the myocardial cell death inhibitory effects of hemin and hematin, wherein hollow rectangle and solid rectangle represent hemin and hematin, respectively.

When the viable cell count in the group with no antibody added was made 1, mean values (±SD) of the viable cell counts in the groups with hemin and hematin added are shown in FIG. 7.

From the foregoing results, it is noted that hemin and hematin exhibit the activity of inhibiting myocardial cell death.

Experimental Example 3

Inhibitory Activity Against Myocardial Cell Death Induced by Doxorubicin

The primary cardiomyocytes derived from rat neonates obtained in EXPERIMENTAL EXAMPLE 2 were suspended in Medium 199 containing 10% fetal cow serum in $6 \times 10^5$ cells/ml, and the suspension was seeded on a 96-well plate in 0.1 ml well, followed by incubation for a day in a $CO_2$ incubator set at 37° C. and 5% $CO_2$. After stirring with a micromixer (manufactured by Taiyo Kagaku Kogyo Co., Ltd.), the plate was washed 3 times with serum-free Medium 199 to remove serum. Medium 199 and a sample to be tested were added thereto, followed by incubation for 3 hours. After the incubation, doxorubicin (DOX: final concentration of 200 µM) was added to the mixture, which was incubated for further 18 hours to induce cell death. Subsequently, fetal cow serum was added thereto to reach 10%. After further incubation in a $CO_2$ incubator set at 37° C. and 5% $CO_2$ for about 17 hours, the viable cell count was determined using a cell count assay kit (manufactured by Dojin Chemical Laboratory) in which WST-8 was used as a chromogen. Thus, the myocardial cell death inhibitory activity was examined. The experiment described above was carried out independently in 3 runs. The viable cell count in each of the experimental groups was named the mean value (±SD) of the viable cell counts in each experimental group, when the viable cell count in the group with no doxorubicin added was made 1.

Figure 3:
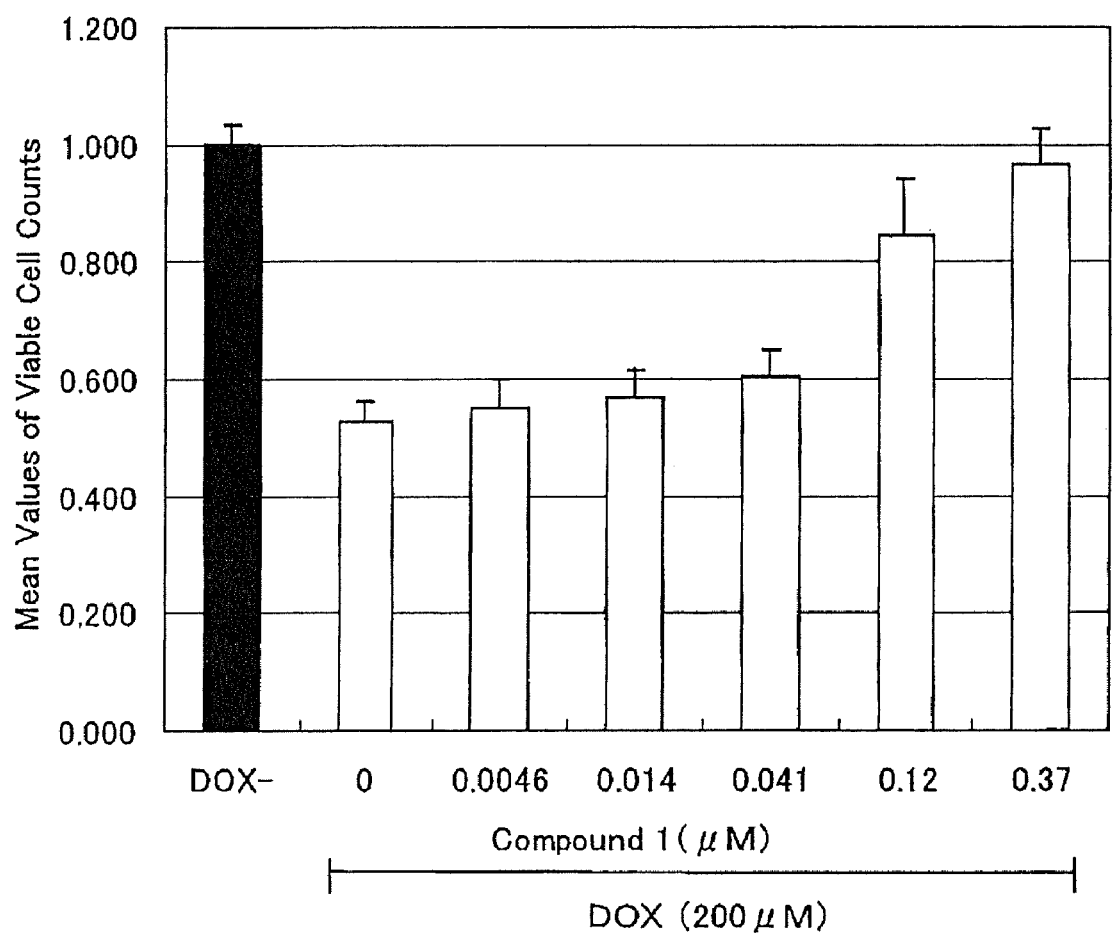
FIG. 3 shows the results of Compound 1 on the inhibitory effects against myocardial cell death induced by doxorubicin (DOX).

The results are shown in FIG. 3.

From the foregoing results, it is noted that Compound 1 exhibits the activity of inhibiting myocardial cell death induced by doxorubicin.

Experimental Example 4

Inhibitory Activity Against Myocardial Cell Death Induced by a Statin

The primary cardiomyocytes derived from rat neonates obtained in EXPERIMENTAL EXAMPLE 2 were suspended in Medium 199 containing 10% fetal cow serum in $6 \times 10^5$ cells/ml, and the suspension was seeded on a 96-well plate in 0.1 mlwell, followed by incubation for a day in a $CO_2$ incubator set at 37° C. and 5% $CO_2$. After stirring with a micromixer (manufactured by Taiyo Kagaku Kogyo Co., Ltd.), the medium was replaced 3 times with serum-free Medium 199 to remove serum. Simvastatin (0.3 µM) or atorvastatin (1 µM) and Compound 1 were added thereto, followed by incubation for further 3 days. Thereafter, fetal cow serum was added thereto to become 10%. After further incubation in a $CO_2$ incubator set at 37° C. and 5% $CO_2$ for about 17 hours, the viable cell count was determined using a cell count assay kit (manufactured by Dojin Chemical Laboratory) in which WST-8 was used as a chromogen, thereby to examine the inhibitory activity of myocardial cell death induced by the statin. The experiment described above was carried out independently in 3 runs. The viable cell count in each of the experimental groups was named the mean value (±SD) of the viable cell counts in each experimental group, when the viable cell count in the group with no statin added was made 1.

Figure 4:
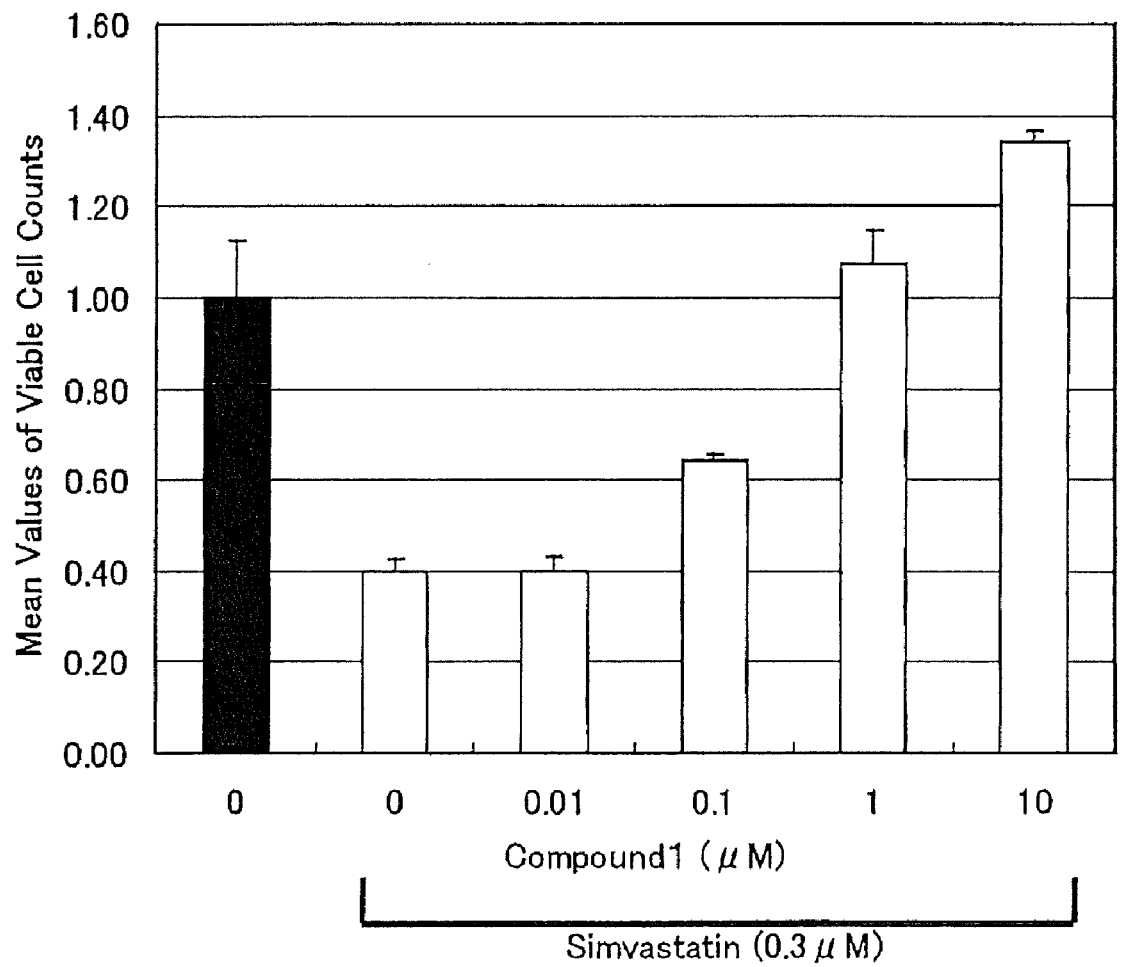
FIG. 4 shows the Compound 1's inhibitory effects against myocardial cell death induced by simvastatin.
Figure 5:
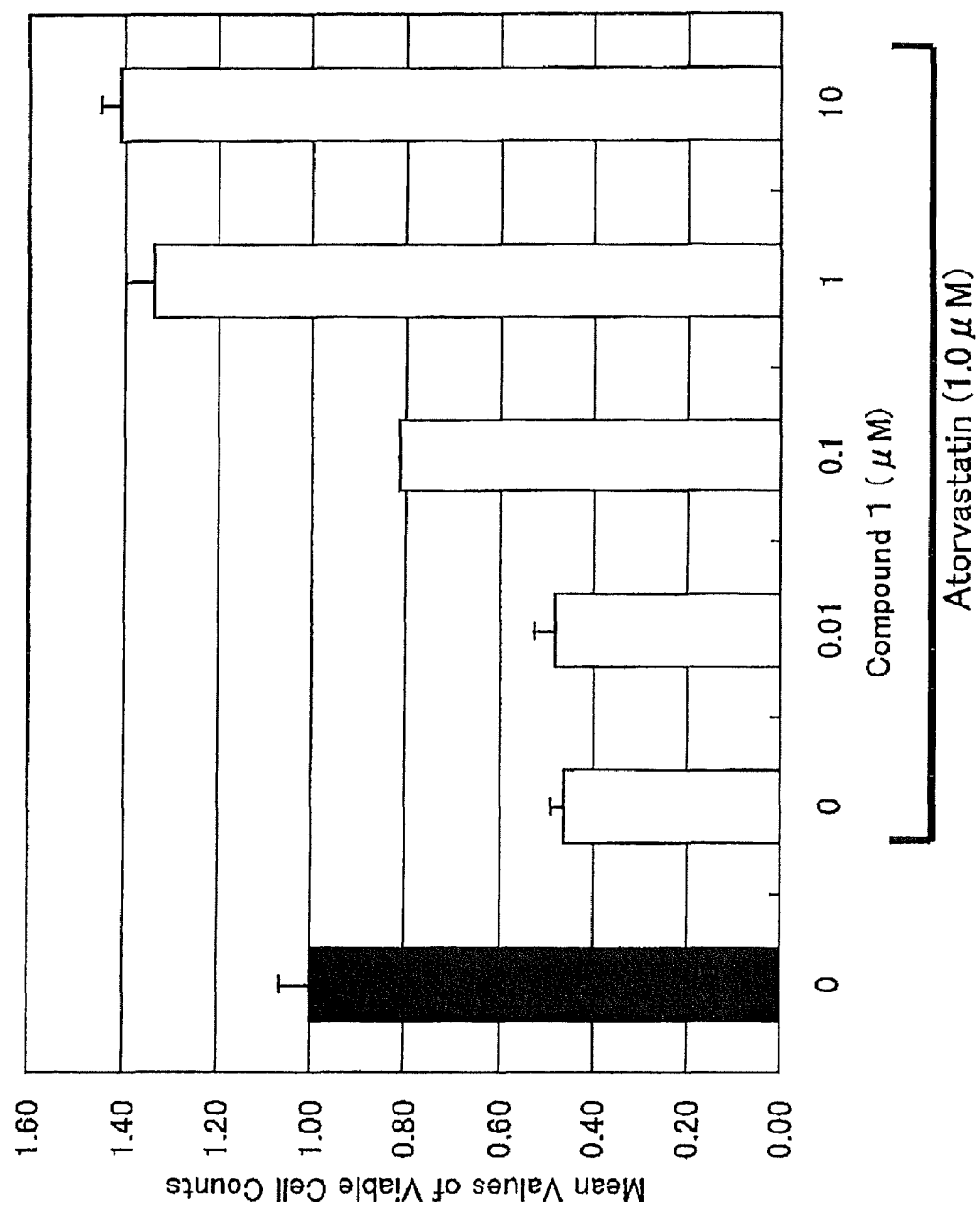
FIG. 5 shows the Compound 1's inhibitory effects against myocardial cell death induced by atorvastatin.

The results are shown in FIG. 4 and FIG. 5.

From the foregoing results, it is noted that simvastatin (0.3 µM) and atorvastatin (1 µM) induce myocardial cell death and further that Compound 1 exhibits the activity of inhibiting myocardial cell death induced by the HMG-CoA reductase inhibitor.

Experimental Example 5

Inhibitory Activity Against Serum Depletion-Induced Cell Death of Vascular Smooth Muscle Normal human umbilical vein endothelial cells (Dainippon Pharmaceutical Co., Ltd.) were suspended in MCDB131 medium (Dainippon Pharmaceutical Co., Ltd.) containing 10% fetal cow serum in $4 \times 10^4$ cells/ml, and the suspension was seeded on a 96-well plate by 0.1 mlwell, followed by incubation for a day in a $CO_2$ incubator set at 37° C. and 5% $CO_2$. After stiffing with a micromixer (manufactured by Taiyo Kagaku Kogyo Co., Ltd.), the medium was removed and serum-free MCDB131 medium and Compound 1 obtained in REFERENCE EXAMPLE 1 were added thereto, followed by incubation for 3 days. After incubation, the viable cell count was determined using a cell count assay kit (manufactured by Dojin Chemical Laboratory) in which WST-8 was used as a chromogen. The inhibitory activity of myocardial cell death was thus examined. The experiment described above was carried out independently in 3 runs. The viable cell count was named the mean value (±SD) of the viable cell counts in each of the groups added in various concentrations, when the viable cell count in the group with no Compound 1 added was made 1.

Figure 6:
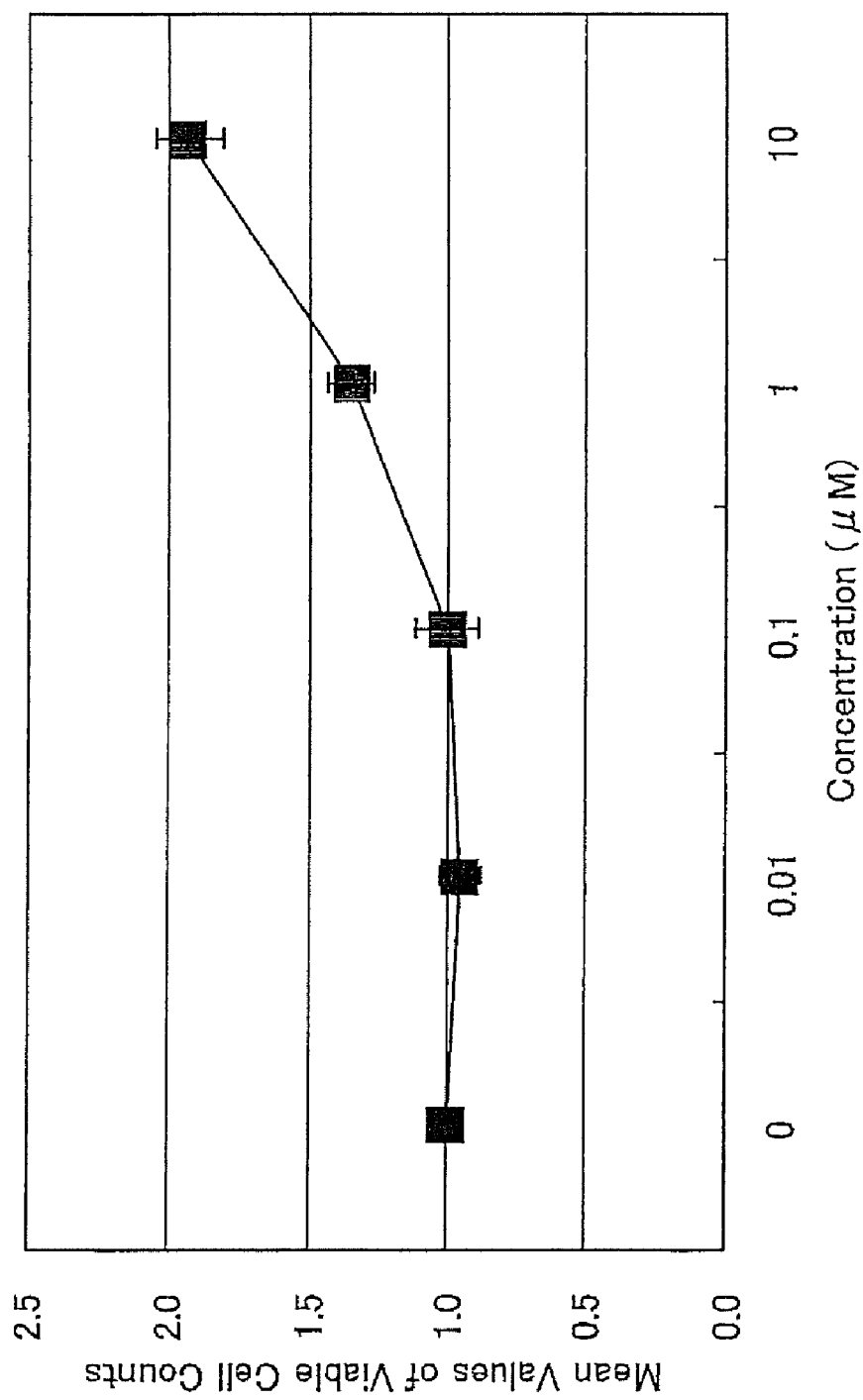
FIG. 6 shows the Compound 1's inhibitory effects against cell death of vascular smooth muscle induced by serum depletion.

The results are shown in FIG. 6.

From the foregoing results, it is noted that Compound 1 exhibits the activity of inhibiting vascular smooth muscle cell death induced by serum depletion.

Experimental Example 6

Inhibitory Activity Against Cell Death of Human Articular Chondrocytes Induced by NO Human normal articular chondrocytes (Clonetics, Inc.) were proliferated in a growth medium for articular chondrocytes (CGM, Clonetics, Inc.) in monolayer culture. Then, the cells were suspended in 1.2% alginate-containing 155 mM NaCl solution in a density of $2.0 \times 10^6$ cells/ml, and beads having a 2 mm diameter were prepared using a syringe with a 22 gauge needle. The beads were incubated in a differentiation medium for articular chondrocytes (CDM, Clonetics, Inc.) charged in a 96-well round-bottomed plate (1 bead/well, manufactured by FALCON) for further 7 days. The medium was replaced by α-modified minimum essential medium containing Compound 1 (0.1 µM or 1 µM) and 10% fetal cow serum, followed by incubation for 48 hours and then for 5 hours in the co-presence of 1.5 mM sodium nitroprusside (NO generator, manufactured by Sigma). As control drugs, caspase 3 inhibitor (Z-DEVD-FMK (SEQ ID NO: 5), 100 µM, manufactured by R & D Systems, Inc.) and caspase 9 inhibitor (Z-LEHD-FMK (SEQ ID NO: 6), 100 µM, manufactured by R & D Systems, Inc.) were similarly monitored for their activities. After completion of the experiment, alginate was removed and the cell survival rate was determined by the MTT technique. The results are shown in TABLE 1.

TABLE 1

| Compound No. (concentration) | Cell Death Inhibition Rate |
|---|---|
| Compound 1 (0.1 µM) | 44.7 ± 0.9 |
| Compound 1 (1 µM) | 57.6 ± 7.0 |
| Z-DEVD-FMK (100 µM) for control (SEQ ID NO: 5) | 49.7 ± 10.3 |
| Z-LEHD-FMK (100 µM) for control (SEQ ID NO: 6) | 62.7 ± 10.6 |

In the table, the numerical values indicate mean values (±SD) of the cell death inhibition rates as converted from the measurement data by the MTT technique. The cell survival rate after the addition of 1.5 mM sodium nitroprusside (without addition of either Compound 1 or control drug) was 31.9%.

It is noted that Compound 1 has the inhibitory activity against the cell death of human articular chondrocytes induced by NO.

Experimental Example 7

Gene Expression Analysis by DNA Chip

The primary cardiomyocytes derived from rat neonates obtained in EXPERIMENTAL EXAMPLE 2 were suspended in Medium 199 containing 10% fetal cow serum in $1.5 \times 10^5$ cells/ml, and the suspension was seeded on a 12-well plate (manufactured by Asahi Techno Glass Corporation) in 2 ml/well, followed by incubation for a day at 37° C. and 5% $CO_2$. After gently stirring, the plate was washed 3 times with Medium 199 medium to remove serum. Medium 199 medium and Compound 1 were added thereto, followed by incubation for 21 hours at 37° C. in 5% $CO_2$. The medium was then removed and total RNA was recovered using RNeasy Mini Kit (manufactured by QIAGEN). Using the total RNA, exhaustive analysis of gene expression was performed on GeneChip arrays for expression analysis (Rat Genome U34A Arrays: manufactured by AFFYMETRIX). The increasing rate of expression of each gene was expressed in terms of the expression level with the addition of the compound, when the expression level without addition of any compound was made 1.

The results are shown in TABLE 2.

TABLE 2

| Gene | Increasing Rate of Expression |
|---|---|
| Heme oxygenase-1 | 2.0 |
| Liver glutathione S-transferase Ya subunit | 11.6 |
| Liver glutathione S-transferase Yc subunit | 2.3 |
| Glutathione S-transferase Yb subunit | 2.5 |
| Glutathione S-transferase Yc1 subunit | 2.1 |
| Gamma-glutamylcysteine synthetase | 2.4 |
| NAD(P)H: quinone reductase | 9.4 |
| UDP-glucuronosyltransferase, exon 1 | 5.0 |
| Bilirunin-specific UDP-glucuronosyltransferase | 5.2 |
| NAD(P)H-menadione oxidereductase | 2.8 |

From the results it is noted that Compound 1 enhances expression of the genes under control of Antioxidant response element (ARE).

Experimental Example 8

Heme Oxygenase-1 Production-Increasing Activity of Compound 1

The primary cardiomyocytes derived from rat neonates, which were obtained in EXPERIMENTAL EXAMPLE 2, were suspended in Medium 199 containing 10% fetal cow serum in $1.5 \times 10^5$ cells/ml, and the suspension was seeded on a 12-well plate (manufactured by Asahi Techno Glass Corporation) in 2 ml each/well, followed by incubation for a day at 37° C. and 5% $CO_2$. The plate was washed 3 times with Medium 199 medium to remove serum. Compound I was added to the plate, followed by incubation for 24 hours at 37° C. and 5% $CO_2$. After completion of the incubation, the cardiomyocytes were washed once with PBS(−), and 100 μl of cell lysis buffer [10 mM Tris(hydroxymethyl)aminomethane, pH 7.4, 150 mM NaCl, 1 mM EDTA.2Na, 1 mM ethylene glycol-bis(β-aminoethylether]-N,N,N',N'-tetraacetic acid, 0.5 mM (p-aminophenyl)methanesulfonyl fluoride hydrochloride, 200 μM sodium β-glycerophosphate n-hydrate, 20 mM NaF, 2 mM sodium diphosphate decahydrate, 10 μg/ml aprotinin, 10 μg/ml leupeptin, 1% Triton X-100, 0.5% Nonidet P40, 0.1% sodium dodesyl sulfate) was added thereto. After the cell debris was scraped from the plate using a cell scraper, the cell lysis buffer was recovered. The recovered cell lysis buffer was mixed with a sample buffer (Tris-SDS-ME Sample Buffer; manufactured by Daiichi Pure Chemicals Co., Ltd.) in an equal volume. The mixture was heat-treated at 95° C. for 5 minutes, followed by SDS polyacrylamide electrophoresis using Multigel (manufactured by Daiichi Pure Chemicals Co., Ltd.). Next, nitrocellulose membrane (Hybond-ECL; manufactured by Amersham Pharmacia Biotech) soaked in a blotting buffer [0.1 M Tris(hydroxymethyl)aminomethane, 0.192 M glycine, 20% ethanol] for at least 10 minutes, blotting filter paper, dialysis membrane and gel were set on Horize-Blot (manufactured by ATTO, Co.) and treated with 100 mA/gel (64 $cm^2$) for an hour to adsorb the protein in the gel onto the nitrocellulose membrane. Thereafter, the nitrocellulose membrane was soaked in a blocking buffer [TTBS buffer (20 mM Tris-HCl, pH 7.6, 0.137 M NaCl, 0.1% Tween-20) containing 5% skimmed milk powders] and stirred at room temperature for an hour for blocking. Next, the nitrocellulose membrane described above was soaked in an anti-HO-1 antibody solution (manufactured by StressGen) diluted 1000-2000-fold with the blocking buffer, followed by reaction at 4° C. for 12 to 18 hours. After completion of the reaction, the nitrocellulose membrane was washed 3 times with TTBS buffer and soaked in horseradish peroxidase-labeled anti-rabbit IgG antibody solution (manufactured by NEW ENGLAND BioLabs) diluted 2000-fold with the blocking buffer. The reaction was carried out at room temperature for an hour. After completion of the reaction, the membrane was washed 3 times with TTBS buffer and the amount of protein was determined using a western blotting detection reagent (ECL+Plus; manufactured by Amersham) and Hyperfilm ECL (manufactured by Amersham). The rate of increasing the heme oxygenase-1 production was expressed by the amount produced with the addition of the compound, when the amount produced without addition of any compound was made 1.

The results are shown in TABLE 3.

TABLE 3

| | Concentration of Compound 1 (μM) | | |
|---|---|---|---|
| | 0 | 0.04 | 0.4 |
| Increasing Rate of Production | 1.0 | 1.6 | 2.5 |

From these results it is noted that Compound 1 increases the production amount of heme oxygenase-1, which is one of the products from the genes under control of Antioxidant response element (ARE).

Example 1

A tablet is prepared in a conventional manner, using Compound 1 (100 mg), lactose (165 mg), corn starch (25 mg), polyvinyl alcohol (4 mg) and magnesium stearate (1 mg).

Example 2

Screening of the Compound Binding to MIF

Rat MIF obtained in REFERENCE EXAMPLE 6 was immobilized on a sensor chip CM5 (manufactured by Biacore Co., Ltd.). Thereafter, phosphate buffered saline (PBS) containing 10 μM of 3-[2-(4-oxo-4H-1,3-benzothiazin-2-yl)-4- pyridyl]propionic acid (the compound of EXAMPLE 308 described in WO 03/020719) was flown over the sensor chip and changes in surface plasmon resonance signal were monitored as the binding of the compound to rat MIF.

Figure 8:
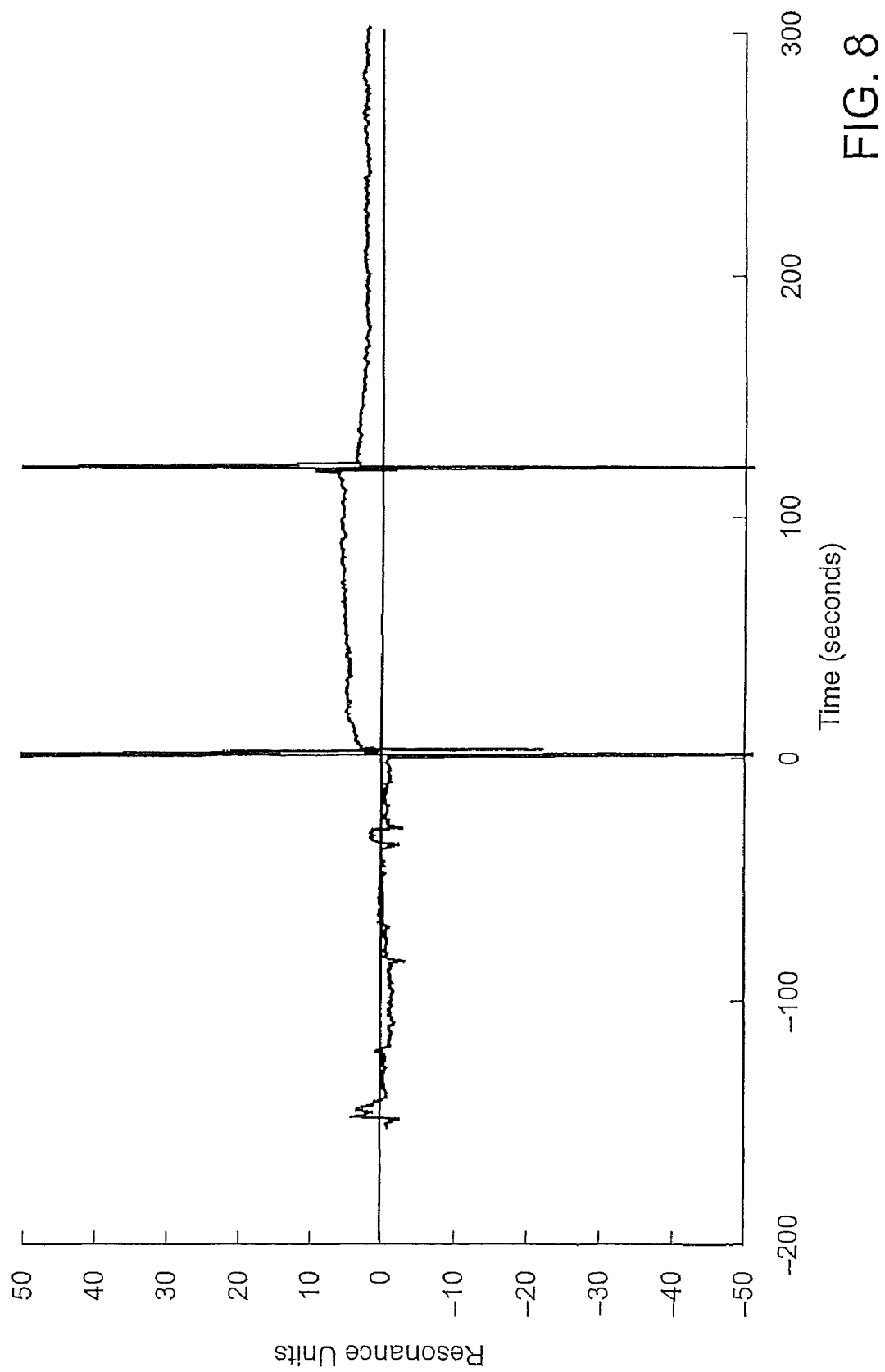
FIG. 8 shows the results of screening a compound binding to MIF, wherein the ordinate represents the surface plasmon resonance signals (resonance units) and the abscissa represents time (seconds).

The results are shown in FIG. 8.

By this, 3-[2-(4-oxo-4H-1,3-benzothiazin-2-yl)-4-pyridyl]propionic acid could be selected as the substance binding to MIF.

INDUSTRIAL APPLICABILITY

The substances capable of binding to macrophage migration inhibitory factor are low toxic and have excellent inhibitory cell death inhibitory effects. The substances inhibit, for example, cell death induced by oxidative stress, cell death induced by serum depletion, cell death induced by deficiency of growth factors, cell death induced by HMG-CoA reductase inhibitors, cell death induced by anticancer agents, cell death induced by NO, cell death induced by amyloid β protein, etc. In addition, these substances promote the expression of genes under control of ARE (e.g., genes of factors for protecting cells from various stresses; etc.), enhance the production of gene proteins (gene products) under control of ARE, or promote their activities. Therefore, the cell death inhibitors of the present invention are useful as agents for the prevention/treatment of, e.g., heart diseases (e.g., myocardiopathy, heart failure, angina pectoris, myocardial infarction, etc.), neurodegenerative diseases (e.g., Parkinson's disease, Alzheimer's disease, triplet repeat disease, prion disease, amyotrophic lateral sclerosis, cerebellar degeneration, retinitis pigmentosa, etc.), cerebrovascular diseases (e.g., cerebral infarction, etc.), central nervous infections (e.g., HIV encephalitis, bacterial meningitis, etc.), traumatic diseases (e.g., spinal cord injury, brain injury, etc.), demyelinating diseases (e.g., multiple sclerosis, etc.), bone/joint diseases (e.g., osteoporosis, arthritis deformans, rheumatism, etc.), kidney diseases (e.g., ischemic acute renal failure, hemolytic uremic syndrome, acute tubular necrosis, hydronephrosis, glomerulonephritis, diabetic nephropathy, etc.), liver diseases (e.g., viral hepatitis, alcoholic hepatitis, etc.), myelodysplastic diseases (e.g., aplastic anemia, etc.), arteriosclerosis, diabetes, pulmonary hypertension, sepsis, inflammatory bowel diseases, autoimmune diseases (e.g., systemic lupus erythematosus, atopic dermatitis, etc.), failure accompanying rejection in organ transplantation, AIDS, cancers (e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.), as protecting agents for transplant organs, etc.

Furthermore, where the cell death inhibitors of the present invention are used in combination with HMG-CoA reductase inhibitors, fibrate-type antihyperlipidemic drugs, anticancer agents or the like, side effects by HMG-CoA reductase inhibitors, fibrate-type antihyperlipidemic drugs, anticancer agents, etc., which give damages to normal cells, are reduced.

Moreover, by screening of the present invention, the substances binding to MIF can be selected efficiently so that the excellent cell death inhibitors of low toxicity can be provided.

The invention claimed is:

1. A method of screening a test compound as a cell death inhibitor, the method comprising determining whether the test compound binds to macrophage migration inhibitory factor, and determining whether the test compound promotes expression of a gene under control of an antioxidant response element selected from the group consisting of Heme oxygenase-1, Liver glutathione S-transferase Ya subunit, Liver glutathione S-transferase Yc subunit, Glutathione S-transferase Yb subunit, Glutathione S-transferase Yc1 subunit, Gamma-glutamylcysteine synthetase, NAD(P)H: quinone reductase, UDP-glucuronosyltransferase, exon 1, Bilirunin-specific UDP-glucuronosyltransferase and NAD(P)H-menadione oxidereductase, wherein binding to macrophage migration inhibitory factor and promoting expression of the gene under control of an antioxidant response element indicates that the test compound is a cell death inhibitor.

2. The screening method according to claim 1, wherein (i) macrophage migration inhibitory factor is mixed with a labeled compound capable of binding to macrophage migration inhibitory factor; and (ii) the test compound and macrophage migration inhibitory factor are mixed with the labeled compound capable of binding to macrophage migration inhibitory factor; and the binding amounts of the labeled compounds bound to the macrophage migration inhibitory factor are measured in each case, and comparison is made therebetween, to thereby determine whether the test compound binds to macrophage migration inhibitory factor.

3. The screening method according to claim 1, wherein the gene under control of an antioxidant response element is heme oxygenase-1.

* * * * *

UNITED STATES PATENT AND TRADEMARK OFFICE
CERTIFICATE OF CORRECTION

PATENT NO. : 8,173,360 B2
APPLICATION NO. : 12/576232
DATED : May 8, 2012
INVENTOR(S) : Haruhide Kimura et al.

Page 1 of 1

It is certified that error appears in the above-identified patent and that said Letters Patent is hereby corrected as shown below:

On the title page:

"item (75) Inventors:", replace "Masayauki Takizawa" with --Masayuki Takizawa--.

Signed and Sealed this
Twelfth Day of February, 2013

Teresa Stanek Rea
*Acting Director of the United States Patent and Trademark Office*

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatgatcata tgcctatgtt catcgtgaac                                          30

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaagaagctc ttccgcaagc gcgaaggtgt ggaaccgttc cag                            43

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatgatcata tgcctatgtt catcgtgaac                                          30
```

```
<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaagaagctc ttccgcaagc gaaggtggaa ccgttccag                          39

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Glu Val Asp
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu His Asp
  1
```